(12) United States Patent
Ostapenko et al.

(10) Patent No.: US 11,506,596 B1
(45) Date of Patent: Nov. 22, 2022

(54) INSPECTION DEVICE AND METHOD

(71) Applicant: Ultrasonic Technologies, Inc., Wesley Chapel, FL (US)

(72) Inventors: Sergei Ostapenko, Wesley Chapel, FL (US); Chad Rodrigues, Wesley Chapel, FL (US); Igor Tarasov, Wesley Chapel, FL (US)

(73) Assignee: ULTRASONIC TECHNOLOGIES, INC., Wesley Chapel, FL (US)

( * ) Notice: Subject to any disclaimer, the term of this patent is extended or adjusted under 35 U.S.C. 154(b) by 120 days.

(21) Appl. No.: 16/825,511

(22) Filed: Mar. 20, 2020

Related U.S. Application Data

(60) Provisional application No. 62/822,776, filed on Mar. 22, 2019.

(51) Int. Cl.
| | | |
|---|---|---|
| *G01N 19/08* | (2006.01) | |
| *G01N 3/20* | (2006.01) | |
| *G01N 3/10* | (2006.01) | |
| *G01N 33/38* | (2006.01) | |

(52) U.S. Cl.
CPC ............ *G01N 19/08* (2013.01); *G01N 3/20* (2013.01); *G01N 3/10* (2013.01); *G01N 33/386* (2013.01); *G01N 2203/0046* (2013.01); *G01N 2203/0258* (2013.01); *G01N 2203/0417* (2013.01)

(58) Field of Classification Search
CPC .... G01N 3/20; G01N 3/10; G01N 2203/0046; G01N 2203/0258; G01N 2203/0417; G01N 33/386; G01N 19/08
See application file for complete search history.

(56) References Cited

U.S. PATENT DOCUMENTS

| | | | | |
|---|---|---|---|---|
| 4,395,917 A | * | 8/1983 | Maltby, Jr. ............... | G01N 3/20 73/838 |
| 6,413,789 B2 | * | 7/2002 | Ostapenko ........ | H01L 21/67253 600/459 |
| 6,581,456 B1 | * | 6/2003 | Clark ...................... | G01N 3/20 271/259 |
| 8,528,407 B2 | * | 9/2013 | Ostapenko .............. | H01L 22/12 73/579 |
| 9,933,394 B2 | * | 4/2018 | Ostapenko ......... | G01N 29/4436 |
| 10,578,613 B2 | * | 3/2020 | Andersson ............ | B01L 3/5085 |
| 2001/0046720 A1 | * | 11/2001 | Ostapenko ........ | H01L 21/67253 257/E21.53 |
| 2003/0126931 A1 | * | 7/2003 | Clark ...................... | G01N 3/20 73/849 |
| 2003/0200815 A1 | * | 10/2003 | Clark ...................... | G01N 3/20 73/849 |

(Continued)

FOREIGN PATENT DOCUMENTS

| | | | |
|---|---|---|---|
| CN | 106769450 A | * 5/2017 | |
| WO | WO-2010121846 A1 | * 10/2010 | ........... B81C 99/005 |

(Continued)

*Primary Examiner* — Jonathan M Dunlap
(74) *Attorney, Agent, or Firm* — Frijouf, Rust & Pyle, P.A.

(57) ABSTRACT

An inspection device and method produces a deformation in a panel body and reveals a defect in the panel body. A base and a collar define a chamber. A vacuum device connects with the chamber for evacuating the chamber after the panel body is positioned adjacent to the collar and deflects the panel body into the chamber for propagating the defect in the panel body.

14 Claims, 19 Drawing Sheets

(56) References Cited

U.S. PATENT DOCUMENTS

| | | | | |
|---|---|---|---|---|
| 2003/0205093 | A1* | 11/2003 | Clark | G01N 3/20 |
| | | | | 73/849 |
| 2004/0217539 | A1* | 11/2004 | Clark | G01N 3/20 |
| | | | | 271/90 |
| 2010/0138027 | A1* | 6/2010 | Ostapenko | G01N 29/348 |
| | | | | 702/56 |
| 2013/0213137 | A1* | 8/2013 | Ostapenko | G01N 29/28 |
| | | | | 73/582 |
| 2015/0059447 | A1* | 3/2015 | Rickards | G01N 11/00 |
| | | | | 73/61.41 |

FOREIGN PATENT DOCUMENTS

| | | | | |
|---|---|---|---|---|
| WO | WO-2014176306 A1 * | 10/2014 | | B01L 3/502 |
| WO | WO-2016051346 A1 * | 4/2016 | | F16N 21/02 |
| WO | WO-2019006482 A1 * | 1/2019 | | B09B 1/00 |

* cited by examiner

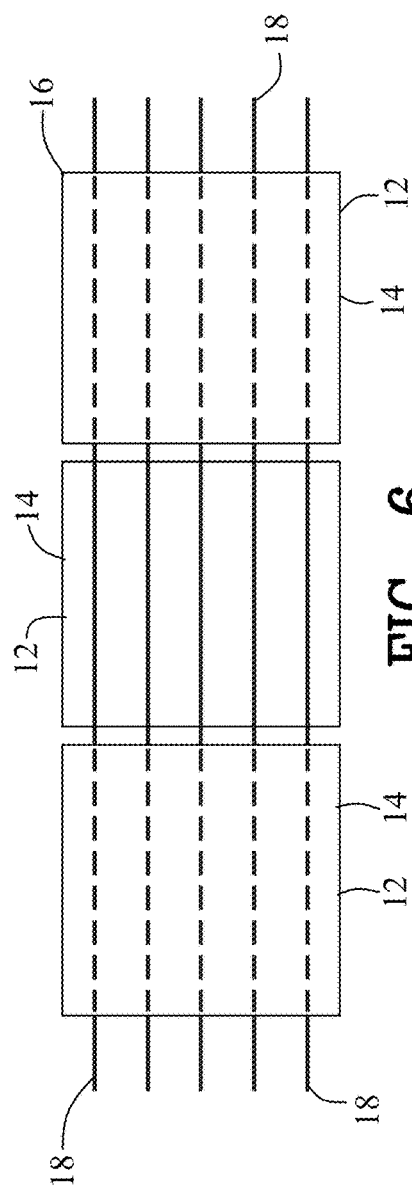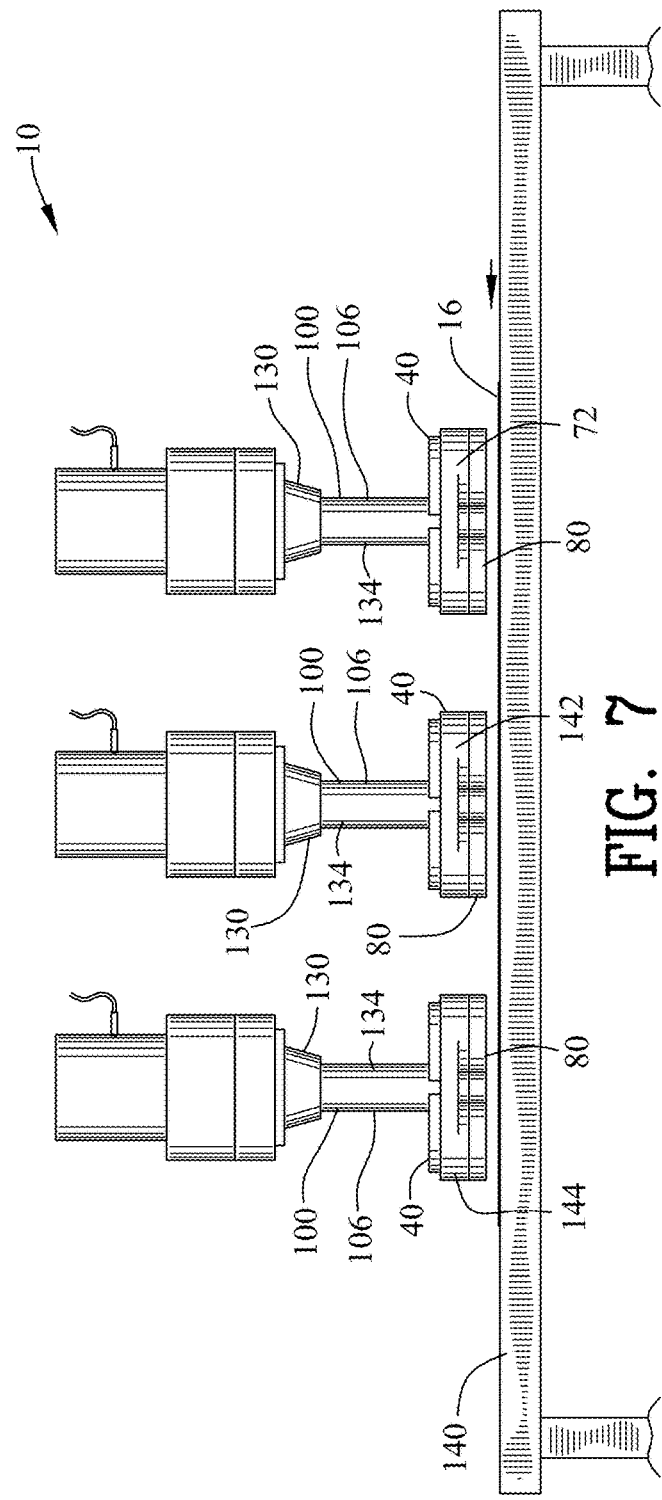

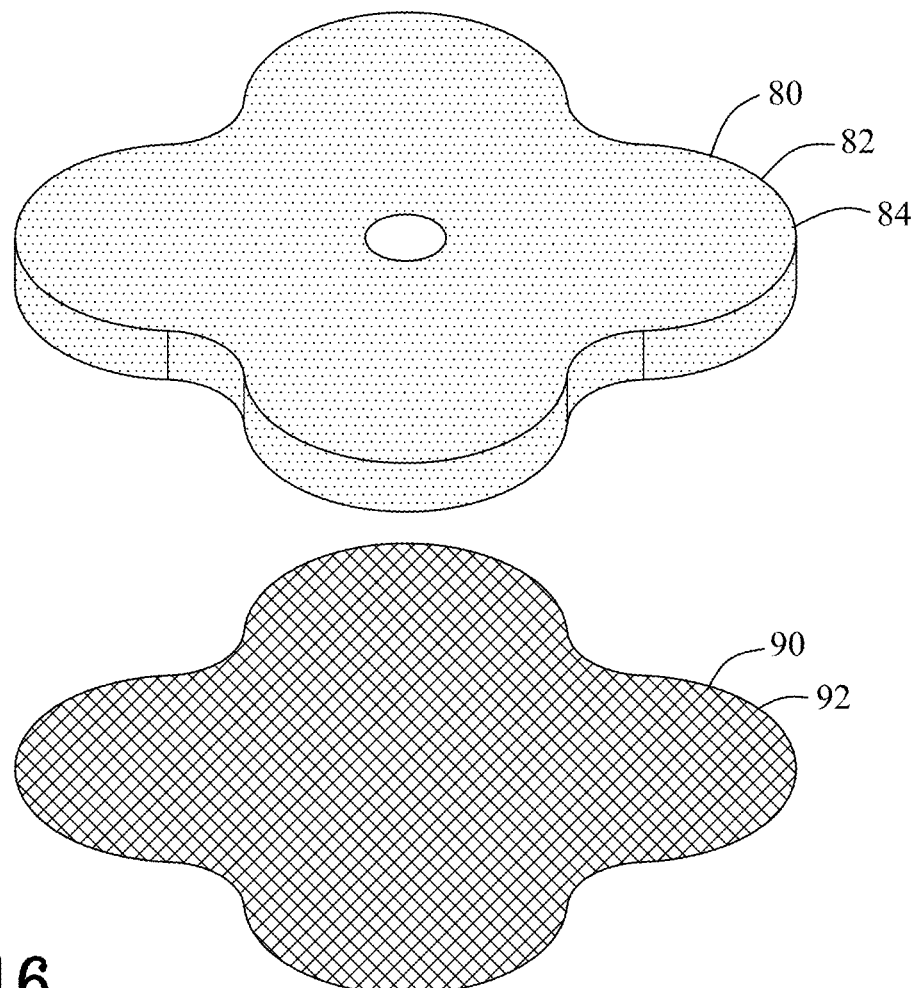
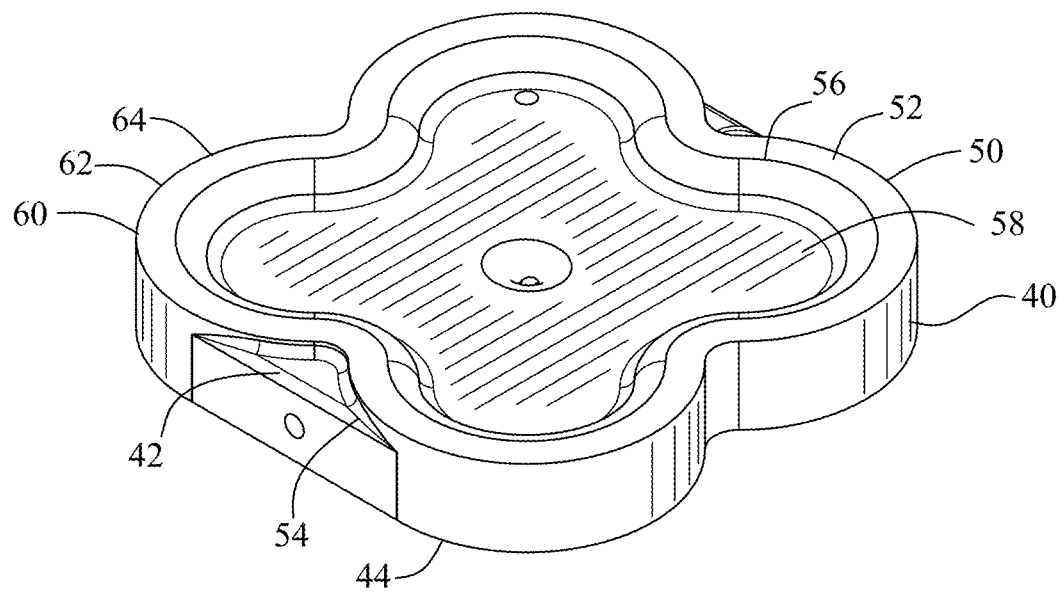
FIG. 16

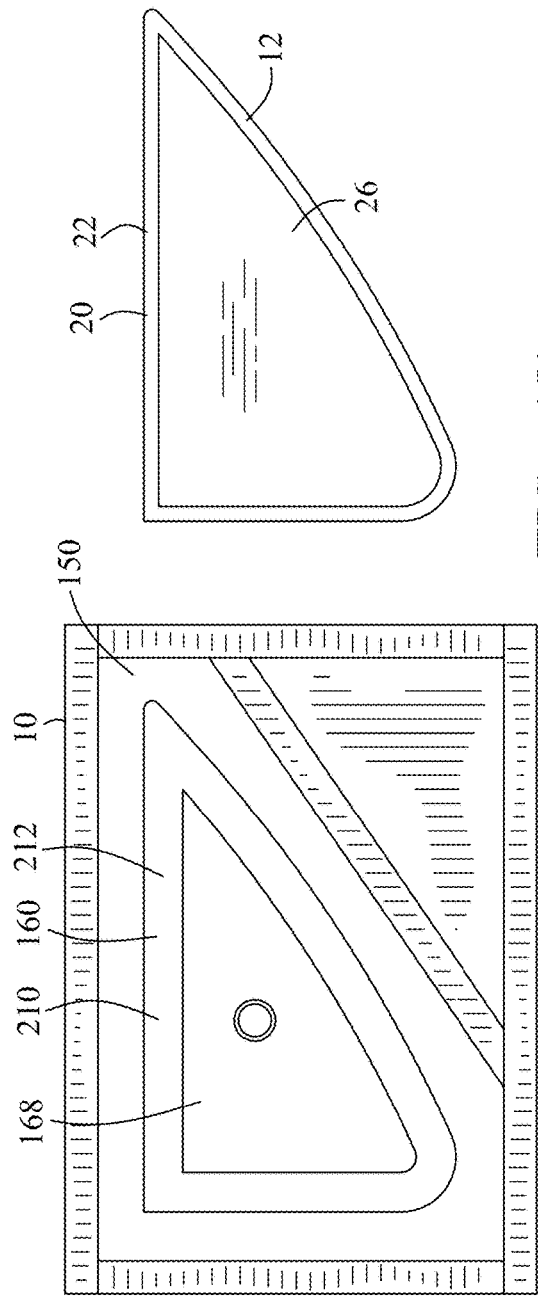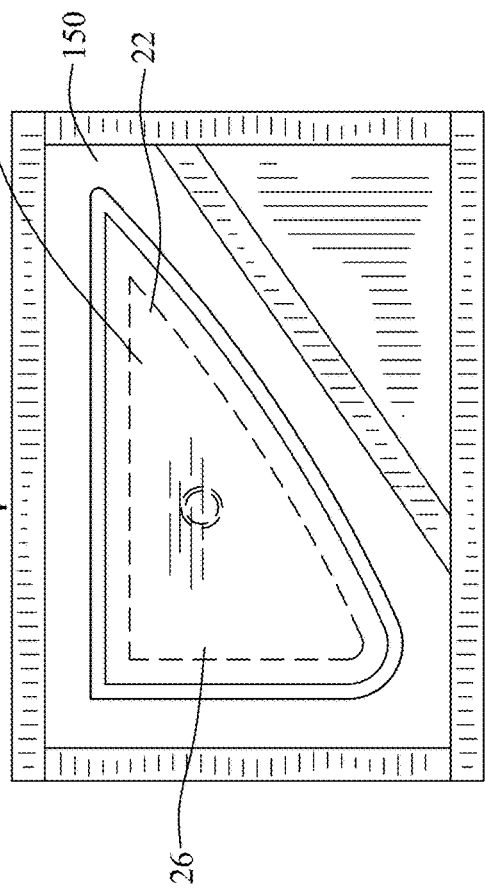
FIG. 17
FIG. 18

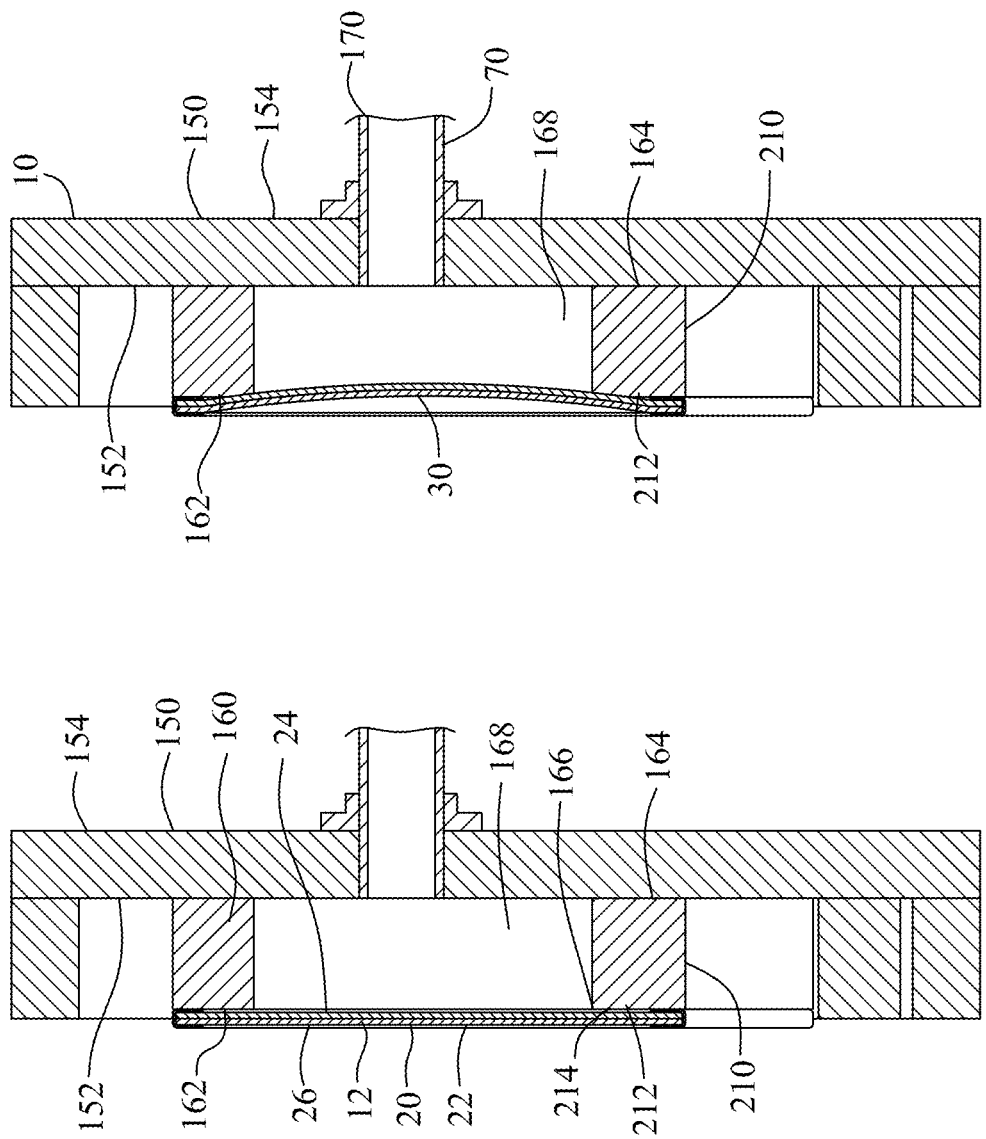

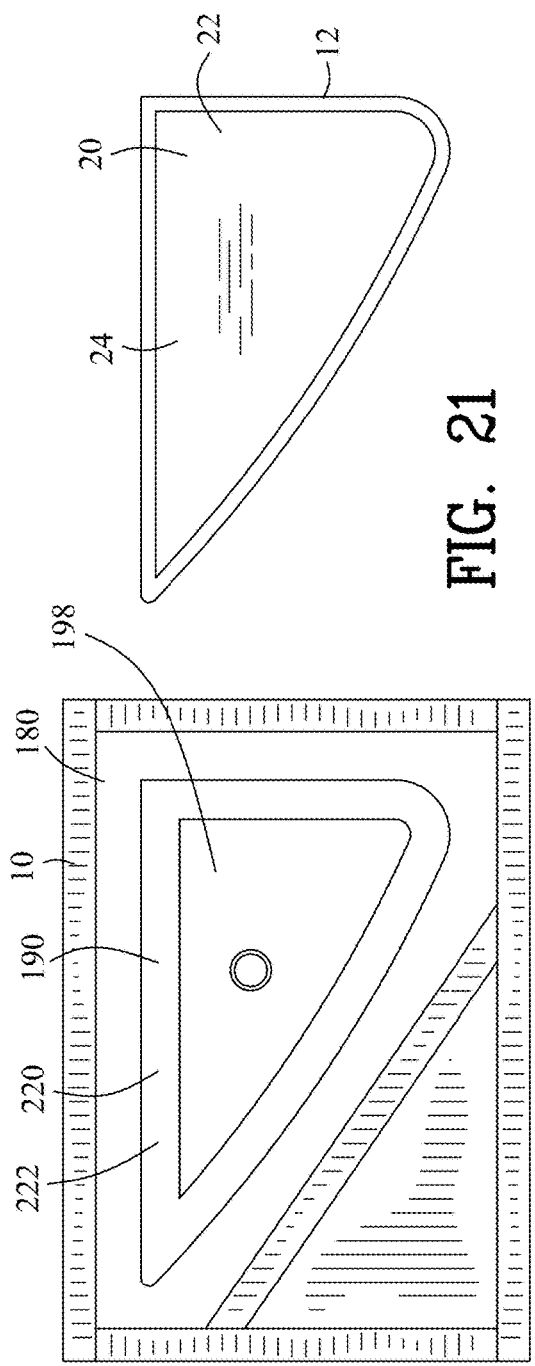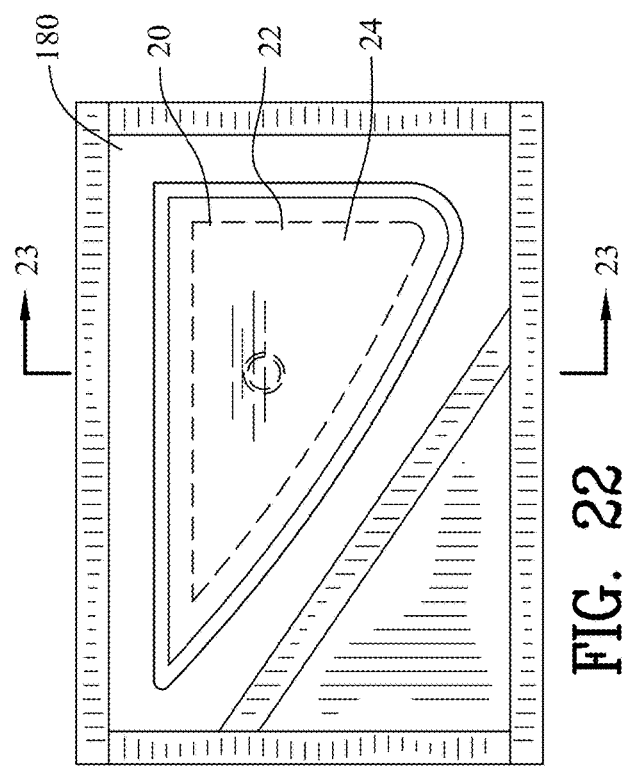
FIG. 21
FIG. 22

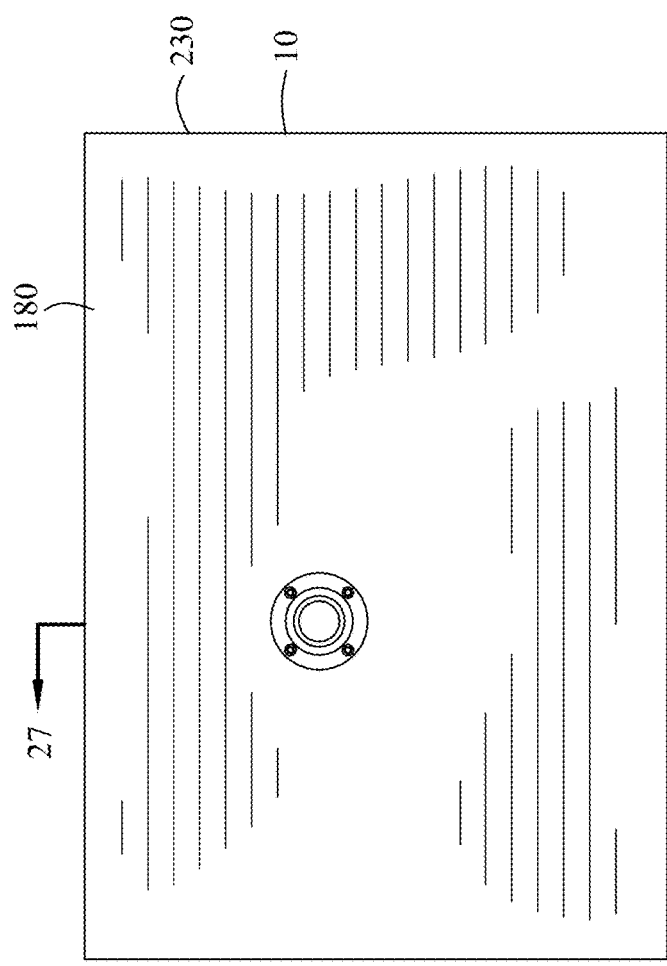
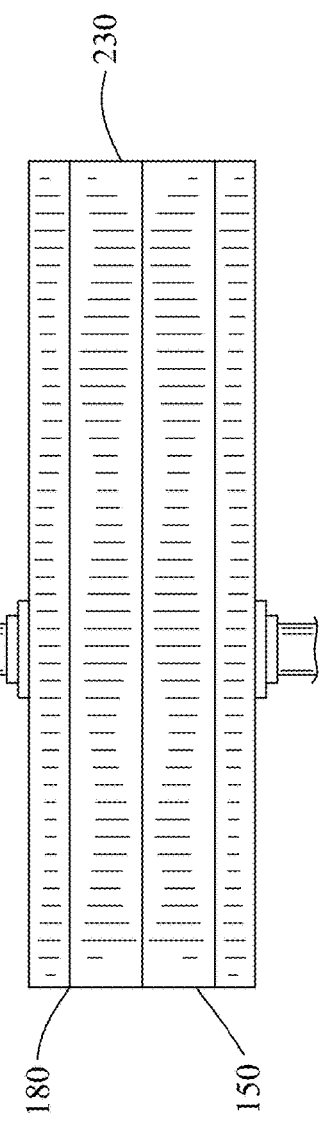

INSPECTION DEVICE AND METHOD

CROSS-REFERENCE TO RELATED APPLICATIONS

This application claims benefit of U.S. Patent Provisional application No. 62/822,776 filed Mar. 22, 2019. All subject matter set forth in provisional application No. 62/822,776is hereby incorporated by reference into the present application as if fully set forth herein.

FIELD OF THE INVENTION

This invention relates to the inspection and more particularly, this invention relates to an inspection device and method for a panel body.

BACKGROUND OF THE INVENTION

Various types of panel bodies are utilized in a multitude of industries including but not limited to electrical, construction, body armor, hardware or other applications. Once these panel bodies are installed it can be extremely time-consuming and expensive to replace them thereafter. An inspection device for inspecting the panel bodies before installation and utilization may be both time-saving and greatly reduce the overall expense of the panel bodies. There is a need for an inspection device for inspecting and determining whether the panel body is defective and therefore discarded before installation and utilization.

Therefore, it is an object of the present invention to provide an inspection device for producing a deformation in a panel body and revealing a defect in the panel body Another object of the present invention is to provide an inspection device that may deform the panel body in multiple angular orientations for increasing the homogeneous stress distribution within the panel body resulting in an increased area of testing for the panel body.

Another object of the present invention is to provide an inspection device that may test solar wafers such as solar cells.

Another object of the present invention is to provide an inspection device that can test multiple panel bodies that are in a string configuration.

Another object of the present invention is to provide an inspection device that can test round shaped electronic wafers such as LiTaO3 wafers.

Another object of the present invention is to provide an inspection device that can test ceramic plates.

Another object of the present invention is to provide an inspection device that may test automobile windshields or windows.

The foregoing has outlined some of the more pertinent objects of the present invention. These objects should be construed as being merely illustrative of some of the more prominent features and applications of the invention. Many other beneficial results can be obtained by modifying the invention within the scope of the invention. Accordingly other objects in a full understanding of the invention may be had by referring to the summary of the invention and the detailed description describing the preferred embodiment of the invention.

SUMMARY OF THE INVENTION

The present invention is defined by the appended claims with the specific embodiments shown in the attached drawings. For the purpose of summarizing the invention, the invention comprises an inspection device for producing a deformation in a panel body and revealing a defect in the panel body. The inspection device includes a base and a collar defining an opening and a chamber. A vacuum device connects with the chamber for evacuating the chamber after the panel body is positioned adjacent to the collar and deflecting the panel body into the chamber for propagating the defect in the panel body.

In a more specific embodiment of the invention, the collar includes a quatrefoil shape for symmetrically deflecting the panel body into the chamber.

In a more specific embodiment of the invention, a deformable material abuts the collar for defining a deflection seal between the collar and the panel body and maintaining a vacuum within the chamber during deflecting the panel body into the chamber.

In one embodiment of the invention, a base displacer positions the panel body between a first engagement position, a non-engagement position and a second engagement position. The first engagement position abuts the panel body with the base for defining a first panel body deflection upon the vacuum device evacuating the chamber. The non-engagement position separates the base relative to the panel body. A base pivot pivots the base relative to the panel body during the non-engagement position for alternating the angular orientation of the base relative to the panel body for defining an alter angular orientation of the base relative to the panel body. The second engagement position abuts the panel body with the base for defining a second panel body deflection upon the vacuum device evacuating the chamber. The first panel body deflection and the second panel body deflection define an increased homogeneous stress distribution within the panel body for increasing the area within the panel body for propagating the defect and reducing the evacuation pressure applied by the vacuum device.

In another embodiment of the invention, the base includes a first angular orientation relative to the panel body. A base displacer displaces the base relative to the panel body. The base displacer converges the base relative to the panel body and the vacuum device evacuates the chamber and deflects the panel body into the chamber for propagating the defect in the panel body. A second base has an upper surface and a lower surface. A second collar has an upper surface, a lower surface and defining an opening. The lower surface of the second collar is coupled to the upper surface of the second base for defining a second chamber. The second base includes a second angular orientation relative to the panel body. A transfer device positions the panel body from the base to the second base. A second base displacer displaces the second base relative to the panel body. The second base displacer converges the second base relative to the panel body and the vacuum device evacuates the second chamber and deflects the panel body into the second chamber for propagating the defect in the panel body. The first angular orientation and the second angular orientation define an increased homogeneous stress distribution within the panel body for increasing the area within the panel body for propagating the defect and reducing the evacuation pressure applied by the vacuum device.

The invention is also incorporated into the method of producing a deformation in a panel body and revealing a defect in the panel body. The method comprising the steps of positioning the panel body adjacent to a collar coupled to a base defining a chamber. The chamber is evacuated for deflecting the panel body into the chamber for propagating the defect in the panel body. The vacuum within the chamber is released for removing the panel body from the chamber. The base is separated relative to the panel body. The panel body is inspected for propagated defects.

In another embodiment of the invention, the inspection device produces a deformation in a panel body and revealing a defect in the panel body, the panel body including a primary panel and a secondary panel. The inspection device comprises a primary base having an upper surface and a lower surface. A primary collar has an upper surface, a lower surface and defines an opening. The lower surface of the primary collar is coupled to the upper surface of the primary base for defining a primary chamber. A vacuum device is connected with the primary chamber for evacuating the primary chamber after the primary panel body is positioned adjacent to the upper surface of the primary collar and deflects the primary panel into the primary chamber for propagating the defect in the panel body. A secondary base has an upper surface and a lower surface. A secondary collar has an upper surface, a lower surface and defines an opening. The lower surface of the secondary collar is coupled to the upper surface of the secondary base for defining a secondary chamber. The vacuum device is connected with the secondary chamber for evacuating the secondary chamber after the secondary panel body is positioned adjacent to the upper surface of the secondary collar and deflects the secondary panel into the secondary chamber for propagating the defect in the panel body.

The invention is also incorporated into the method of producing a deformation in a panel body and revealing a defect in the panel body. The panel body includes a primary panel and a secondary panel. The method comprising the steps of positioning the primary panel adjacent to a primary collar coupled to a primary base defining a primary chamber. The primary chamber is evacuated for deflecting the primary panel into the primary chamber for propagating the defect in the primary panel. The vacuum is released within the primary chamber for removing the primary panel from the primary chamber. The secondary panel is positioned adjacent to a secondary collar coupled to a secondary base defining a secondary chamber. The secondary chamber is evacuated for deflecting the secondary panel into the secondary chamber for propagating the defect in the secondary panel. The vacuum is released within the secondary chamber for removing the secondary panel from the secondary chamber. The panel body is inspected for propagated defects.

The foregoing has outlined rather broadly the more pertinent and important features of the present invention in order that the detailed description that follows may be better understood so that the present contribution to the art can be more fully appreciated. Additional features of the invention will be described hereinafter which form the subject matter of the invention. It should be appreciated by those skilled in the art that the conception and the specific embodiments maybe modified for carrying out the same purposes of the present invention. It should also be realized by those skilled in the art that such equivalent constructions do not depart from the spirit and scope of the invention.

BRIEF DESCRIPTION OF THE DRAWINGS

For a fuller understanding of the nature and objects of the invention, reference should be made to the following detailed description taken in connection with the accompanying drawings in which:

FIG. 6 is a top view of a plurality of wafers electrically coupled by a plurality of electrical ribbons;

FIG. 7 is a third embodiment of an inspection device for a plurality of panel bodies of the present invention;

FIG. 16 is an exploded view of a base, a screen and a deformable material;

FIG. 17 is a fourth embodiment of an inspection device having a primary base for testing a panel body having a primary panel;

FIG. 18 is a view similar to FIG. 17 illustrating the primary panel engaging with the primary base;

FIG. 19 is a sectional view along line 19-19 in FIG. 18;

FIG. 20 is a view similar to FIG. 19 illustrating the vacuum device evacuating a primary chamber and deflecting the primary panel;

FIG. 21 is a similar view to FIG. 17 illustrating the inspection device having a secondary base for testing a panel body having a secondary panel;

FIG. 22 is a view similar to FIG. 21 illustrating the secondary panel engaging with the secondary base;

FIG. 25 is a top view of a fifth embodiment of an inspection device having a plurality of abutting layers for testing a panel body having a primary panel and a second panel;

FIG. 26 is a front view of FIG. 25;

Similar reference characters refer to similar parts throughout the several Figures of the drawings.

DETAILED DISCUSSION

Figure 1:
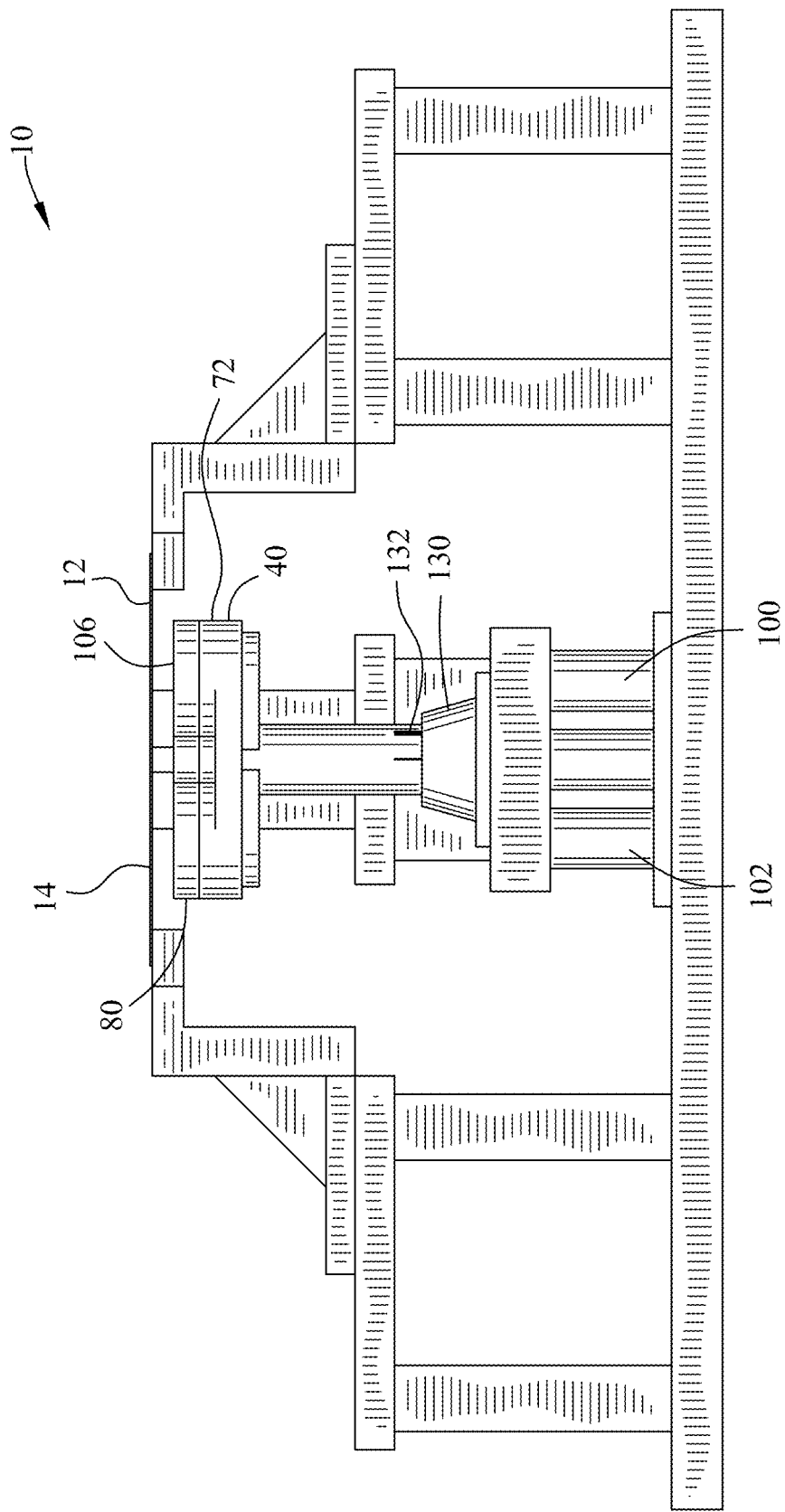
FIG. 1 is an elevated view of a first embodiment of an inspection device for a panel body of the present invention.

FIGS. 1-29 illustrate an inspection device 10 for producing a deformation 30 in a panel body 12 and revealing a defect 32 in the panel body 12. The defect 32 may include cracks, weakened areas or other imperfections within the panel body 12. The defect 32 may be visible or non-visible to the human eye.

The panel body 12 may include a solar wafer 14 as shown in FIGS. 1-5 and 13-15. For example, the solar wafer 14 may include solar cells (Si). The panel body 12 may also include a plurality of solar wafers 16 that are connected by ribbons 18 as shown in FIGS. 6-10. The panel body 12 may alternatively include a ceramic plate, for example a ceramic plate used in solid oxide fuel cells (SOFC). The panel body 12 may alternatively include round shaped electronic wafers such as LiTaO3 (LT) wafer, LiNbO3 wafer, GaAs wafer, GaN wafer or other electronic waters.

The panel body 12 may include glass 20. For example, the glass 20 may include an automobile windshield or window 22 as shown in FIGS. 17-29. An automobile windshield or window 22 includes a primary panel 24 and a secondary panel 26 mated together to form safety glass. The panel body 12 may include other panel bodies or plate bodies.

The inspection device 10 includes a base 40 having an upper surface 42 and a lower surface 44. A collar 50 has an upper surface 52, a lower surface 54 and defining an opening 56. The lower surface 54 of the collar 50 is coupled to the upper surface 42 of the base 40 for defining a chamber 58. Preferably the base 40 and the collar 50 are constructed of an integral one piece unit constructed from a polymeric, metallic or other rigid or semi rigid materials. The combination of the base 40 and the collar 50 may be characterized as a chuck 72.

As best shown in FIGS. 2, 3, 5, 9, 20, 24, 28 and 29, a vacuum device 70 connects with the chamber 58 for evacuating the chamber 58 after the panel body 12 is positioned adjacent to the upper surface 52 of the collar 50 and deflecting the panel body 12 into the chamber 58 for propagating the defect in the panel body 12. More specifically, the vacuum device 70 causes a negative pressure within the chamber 58 for drawing the panel body 12 within the chamber 58.

The collar 50 may include a quatrefoil shape 60 for symmetrically deflecting the panel body 12 into the chamber 58. The collar 50 may be constructed from a deformable material 62 for defining a deflection seal 64 between the collar 50 and the panel body 12 for maintaining a vacuum within the chamber 58 during deflecting the panel body 12 into the chamber 58.

Alternatively, a deformable material 62 may abut the upper surface 52 of the collar 50. For example, the deformable material 62 may include a deformable layer 80 constructed from a closed or opened porosity such as extra soft cellular silicones. One such example is produced by Rogers Corporation model BF—1000. The deformable layer 80 defines a deflection seal 82 between the collar 50 and the panel body 12 for maintaining a vacuum within the chamber 58 during deflecting the panel body 12 into the chamber 58.

Preferably, the deformable layer 80 includes a quatrefoil shape 84 for symmetrically sealing between the collar 50 and the panel body 12 for maintaining a vacuum within the chamber 58 during deflecting the panel body 12 into the chamber 58.

As best shown in FIG. 16, the inspection device 10 may further include a screen 90 abutting the upper surface 52 of the collar 50 for retaining any fragments of the panel body 12 that were separated from the panel body 12 during deflection and preventing the fragments from entering the chamber 58 and the vacuum device 70. More specifically, the screen 90 may be positioned between the collar 50 and the deformable layer 80. Preferably, the screen 90 includes a quatrefoil shape 92 for symmetrically sealing between the collar 50 and the panel body 12 for maintaining a vacuum within the chamber 58 during deflecting the panel body 12 into the chamber 58.

As best shown in FIGS. 1-3 and 7-10, the inspection device 10 may further include a base displacer 100 displaces the base 40 relative to the panel body 12. The base displacer 100 may include one or more pneumatic cylinders 102 vertically displacing the base 40 relative to the panel body 12. The base displacer 100 displaces the base 40 relative to the panel body 12 between an engagement position between the base 40 and the panel body 12 as shown in FIGS. 2, 3, 5, 8, 9 and 10 and a disengagement positioned as shown in FIGS. 1, 4 and 7 between the base 40 and the panel body 12.

Figure 2:
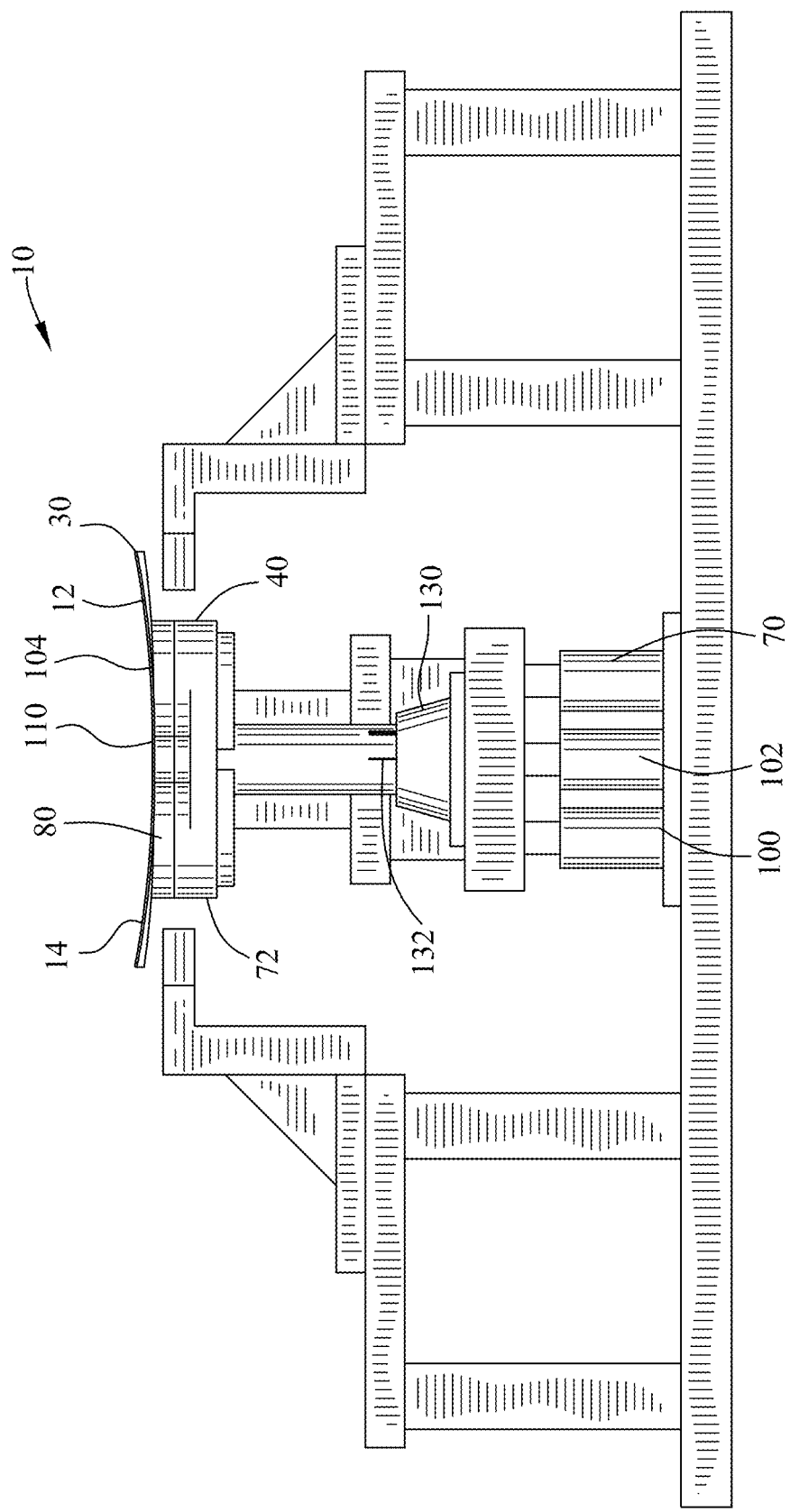
FIG. 2 is a view similar to FIG. 1 illustrating the inspection device producing a deformation in the panel body.
Figure 3:
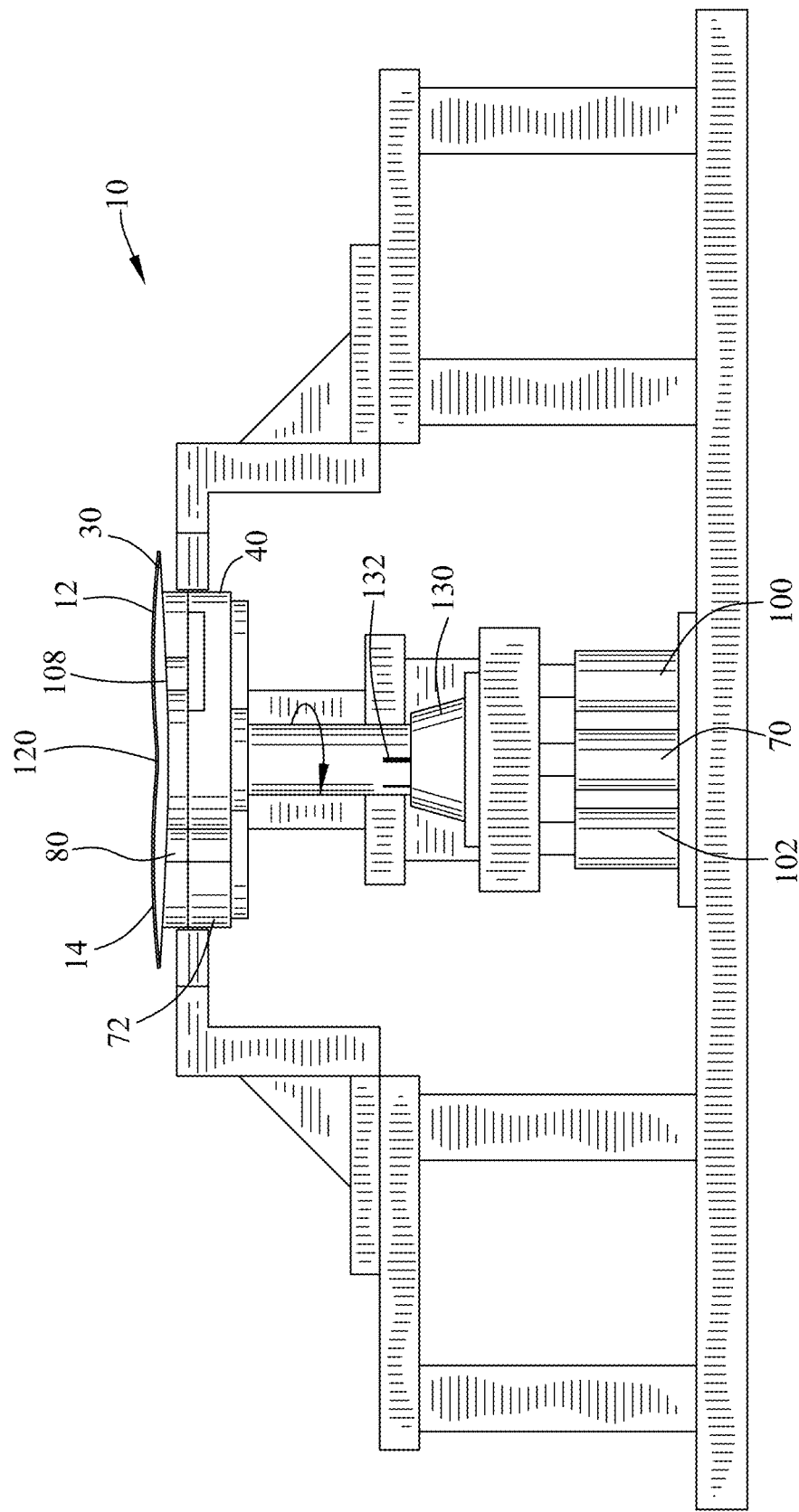
FIG. 3 is a view similar to FIG. 2 illustrating a base of the inspection device having an altered angular orientation relative to the panel body and producing a deformation in the panel body.
Figure 4:
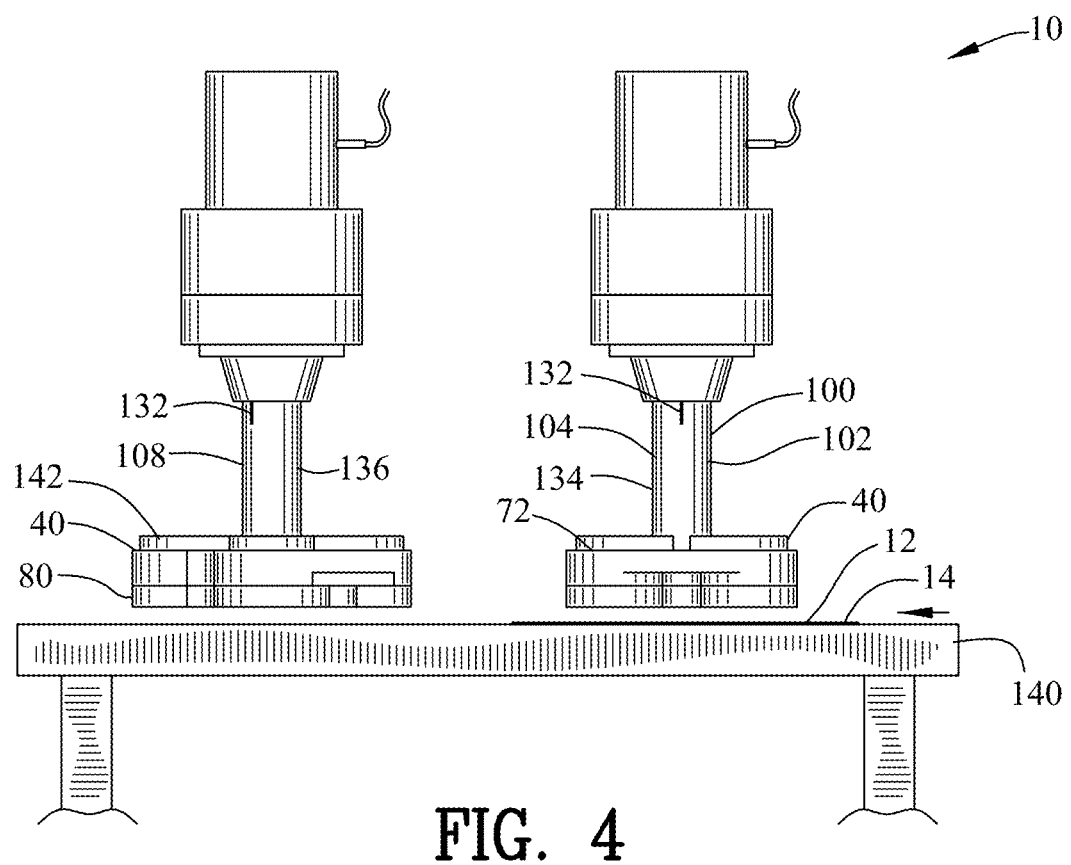
FIG. 4 is a second embodiment of an inspection device for a panel body of the present invention.
Figure 8:
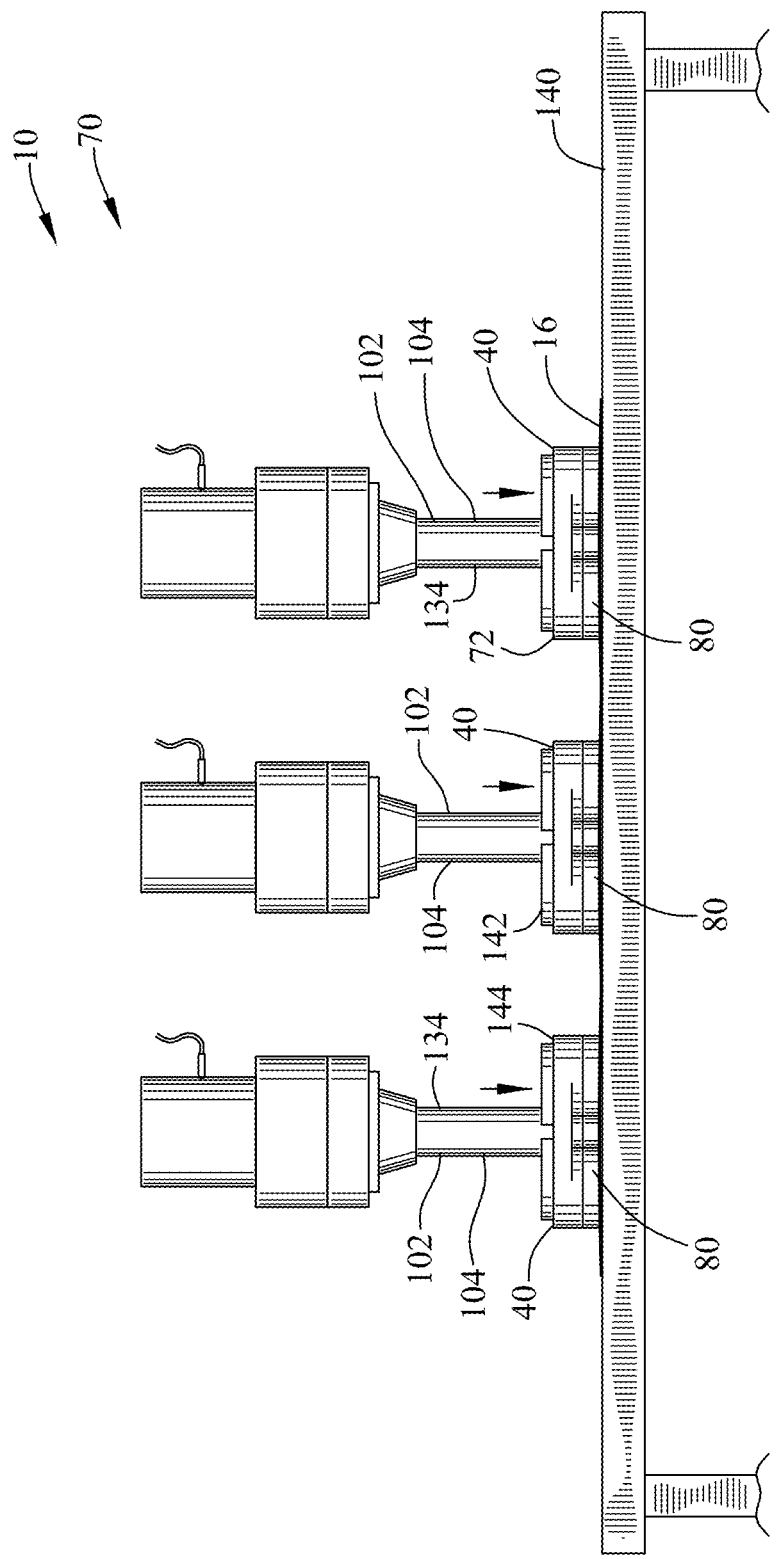
FIG. 8 is a view similar to FIG. 7 illustrating a plurality of bases being displaced for engaging with a plurality of panel bodies.
Figure 9:
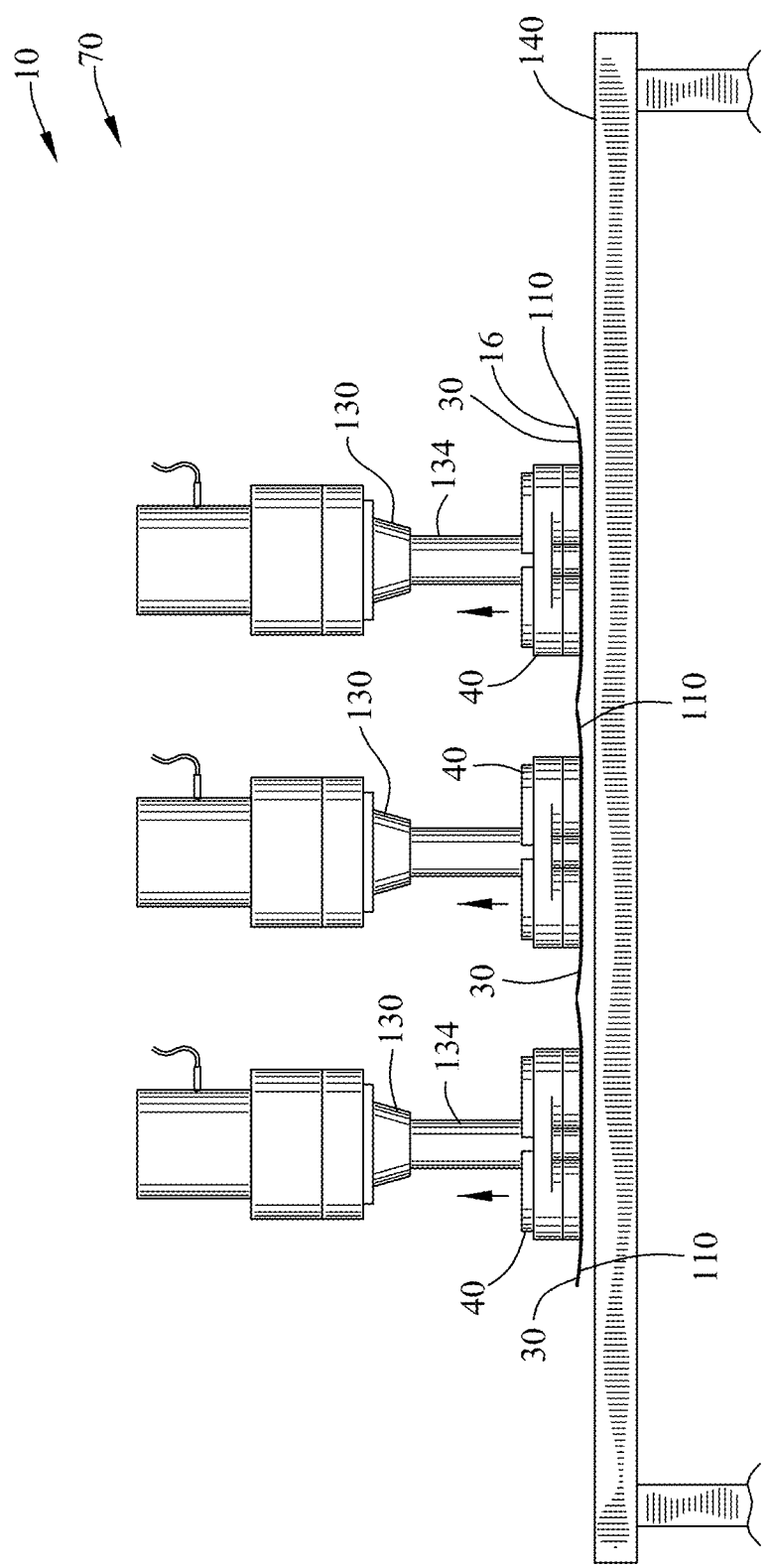
FIG. 9 is a view similar to FIG. 8 illustrating a vacuum device producing a deformation in the plurality of panel bodies.
Figure 10:
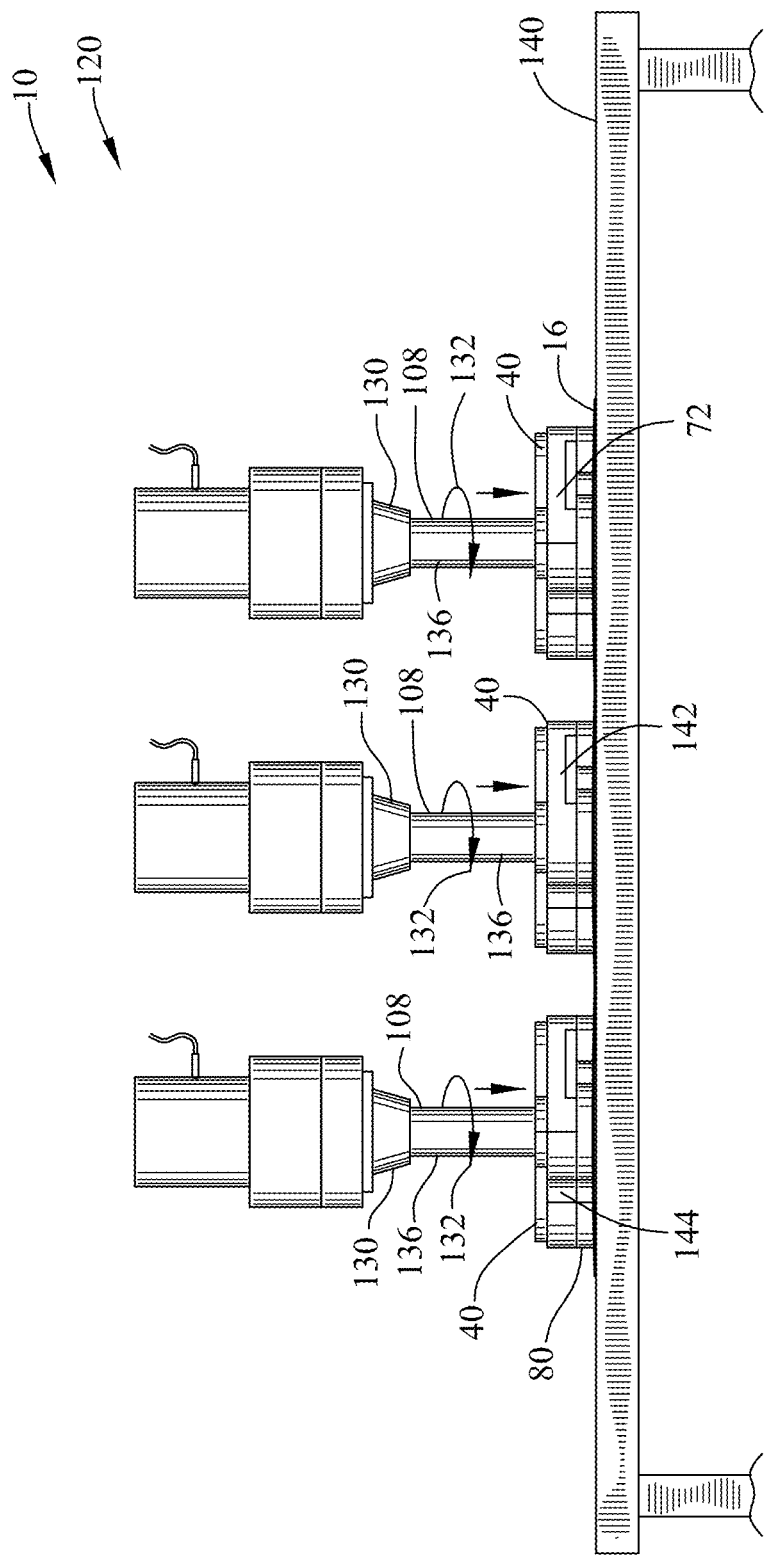
FIG. 10 is a view similar to FIG. 8 illustrating a vacuum device producing a deformation in the plurality of panel bodies.

As best shown in FIGS. 1-3 and 7-10, the inspection device 10 may further include a base pivot 130 for pivoting the base 40 relative to the panel body 12 during the base displacer 100 separating the base 40 relative to the panel body 12 for defining an alter angular orientation 132 of the base 40 relative to the panel body 12. The base displacer 100 converges the base 40 relative to the panel body 12 and the vacuum device 70 evacuates the chamber 58 and deflects the panel body 12 into the chamber 58 for propagating the defect in the panel body 12. More specifically, the base displacer 100 positions the panel body 12 between a first engagement position 104 as shown in FIGS. 2 and 8, a non-engagement position 104 as shown in FIGS. 1 and 7 and a second engagement position 108 as shown in FIGS. 3 and 10.

Figure 11:
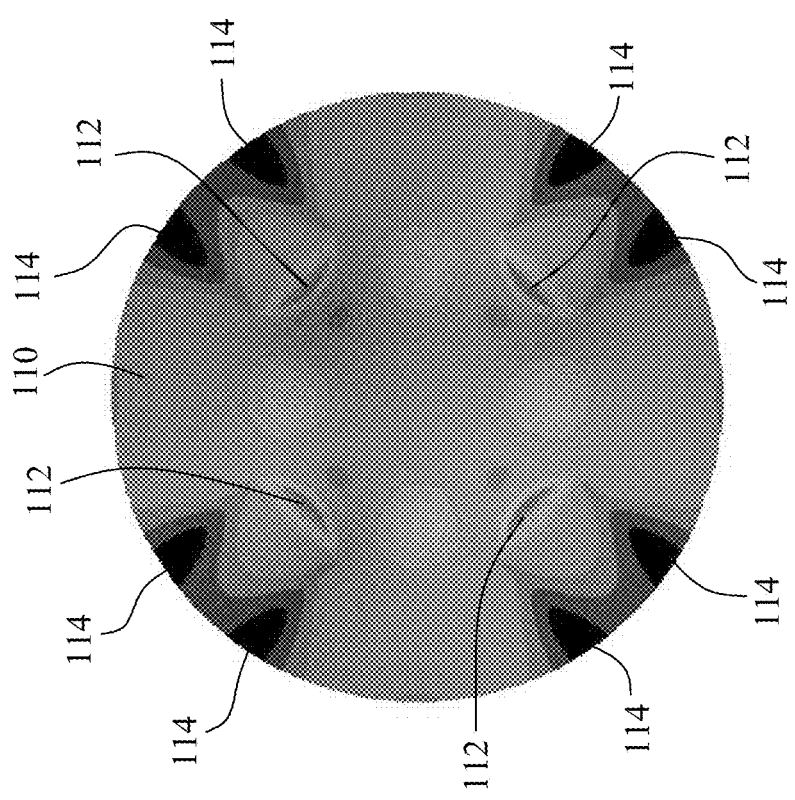
FIG. 11 is a first stress profile generated by the inspection device in a panel body.
Figure 14:
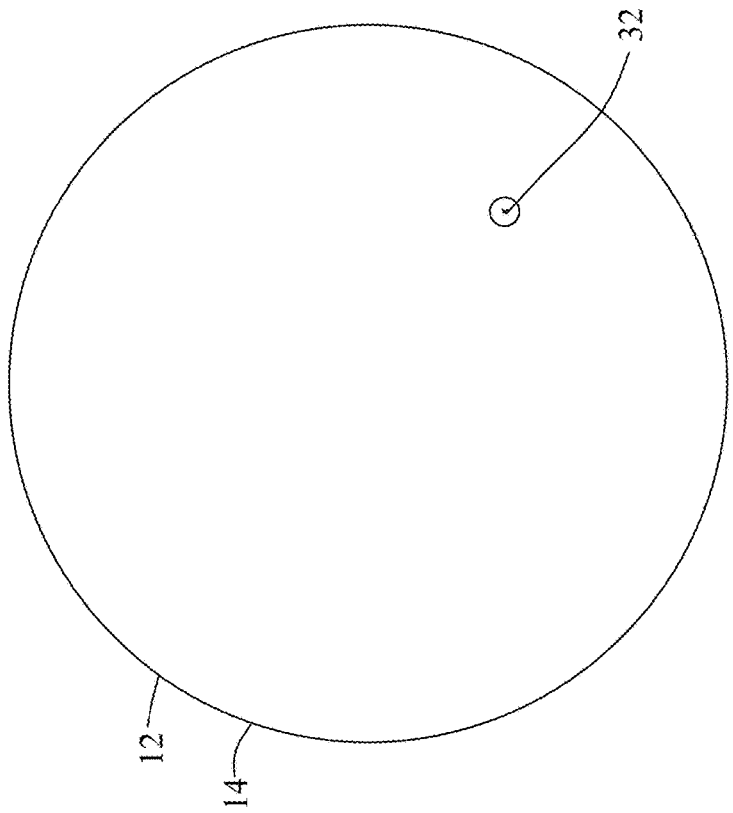
FIG. 14 is an enlarged view of the panel body in FIG. 13 illustrating a propagated defect in the panel body created by the inspection device.
Figure 15:
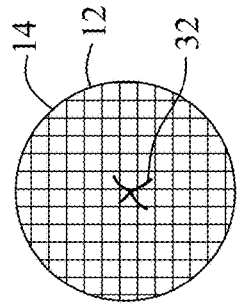
FIG. 15 is an enlarged view of the panel body in FIG. 14 illustrating the propagated defect in the panel body created by the inspection device.
Figure 13:
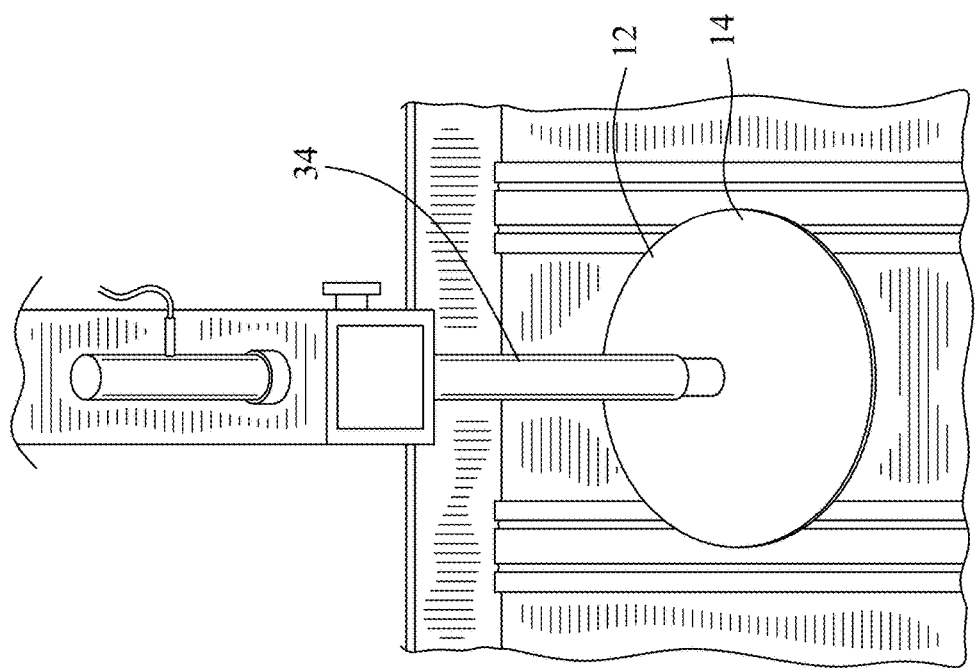
FIG. 13 is a top view of a panel body following the inspection device producing a deformation in the panel body and the panel body being inspected for propagated defects.

The first engagement position 104 abuts the panel body 12 with the base 40 for defining a first panel body deflection 110 upon the vacuum device 70 evacuating the chamber 58. FIG. 11 illustrates the stress distribution on the panel body 12 for the first panel body deflection 110. As shown in FIG. 11, zones 112 represent high stress areas which are responsible for breakage of good panel bodies 12. Zones 114 in FIG. 11 represent very low stress areas or blind spots where no deformation in the panel body 12 occurs and therefore not revealing defects that may be present in the panel body 12.

The non-engagement position 106 separates the base 40 relative to the panel body 12. As shown in FIGS. 3 and 10, the base pivot 130 pivots the base 40 relative to the panel body 12 during the non-engagement position 106 for alternating the angular orientation of the base 40 relative to the panel body 12 for defining an alter angular orientation 132 of the base 40 relative to the panel body 12.

Figure 12:
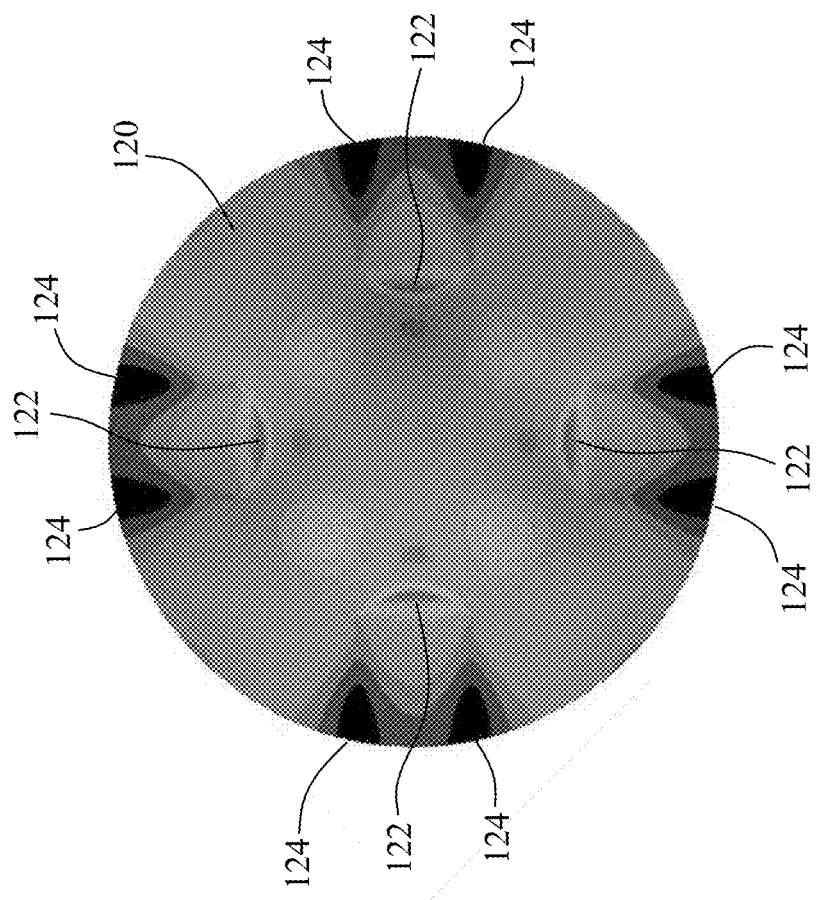
FIG. 12 is a second stress profile generated by the inspection device in the panel body with an altered angular orientation.

The second engagement position 108 abuts the panel body 12 with the base 40 for defining a second panel body deflection 120 upon the vacuum device 70 evacuating the chamber 58. FIG. 12 illustrates the stress distribution on the panel body 12 for the second panel body deflection 120. As shown in FIG. 12, zones 122 represent high stress areas which are responsible for breakage of good panel bodies 12. Zones 124 in FIG. 12 represent very low stress areas or blind spots where no deformation in the panel body 12 occurs and therefore not revealing defects that may be present in the panel body 12.

By testing the panel body 12 with the combination of the first panel body deflection 110 and the second panel body deflection 120, the inspection device 10 increases the homogeneous stress distribution within the panel body for increasing the area within the panel body for propagating the defect and reducing the evacuation pressure applied by the vacuum device. By utilizing a reduced evacuation pressure applied by the vacuum device, the inspection device 10 avoids damaging the panel body 12.

The inspection device 10 may further utilize the base pivot 130 for pivoting the base 40 relative to the panel body 12 for defining a plurality of alter angular orientations of the base 40 relative to the panel body 12. More specifically, the angular orientations of the base 40 relative to the panel body 12 may include zero degrees (0), twenty-two point five degrees (22.5) and forty-five degrees (45). The inspection device 10 may further include a third panel body deflection by positioning the base 40

FIGS. 7-10 illustrate the inspection device 10 utilizing a plurality of bases 40 and collars 50 for testing a plurality of panel bodies 12. More specifically, the inspection device 10 may include a first chuck 72, a second chuck 142 and a third chuck 144 for simultaneously testing plurality of panel bodies 12. The plurality of panel bodies 12 may include a plurality of solar wafers 16 coupled by ribbons 18. A transfer device 140 may be used to conveying the plurality of panel bodies 12 into position under the collar 50. The transfer device 140 may include a belt conveyor or other conveying devices.

The inspection device 10 in FIGS. 7-10 utilizes a base pivot 130 for each of the bases 40. The sequence for utilizing the inspection device 10 as illustrated in FIGS. 7-10 would include first positioning the plurality of panel bodies 12 beneath the plurality of bases 40 and collars 50 as shown in FIG. 7. The base displacer 100 of each of the plurality of bases 40 and collars 50 would next be utilized to abut each of the collars 50 with each of the panel bodies 12 as shown in FIG. 8. As shown in FIG. 9 the base displacer 10 would be utilized for elevating the plurality of bases 40 and collars 50 above the transfer device 140 and the vacuum device 70 would be activated for deforming the panel bodies 12. Thereafter the panel bodies 12 would be lowered to the transfer device 140 and the vacuum device 70 would be disengaged as shown in FIG. 7. Each of the plurality of bases 40 would be rotated by the pace pivots 134 changing the orientation of the collar 50 relative to the panel body 12 as shown in FIG. 10. Thereafter, as shown in FIG. 9 the base displacer 10 would be utilized for elevating the plurality of bases 40 and collars 50 above the transfer device 140 and the vacuum device 70 would be activated for deforming the panel bodies 12.

Figure 5:
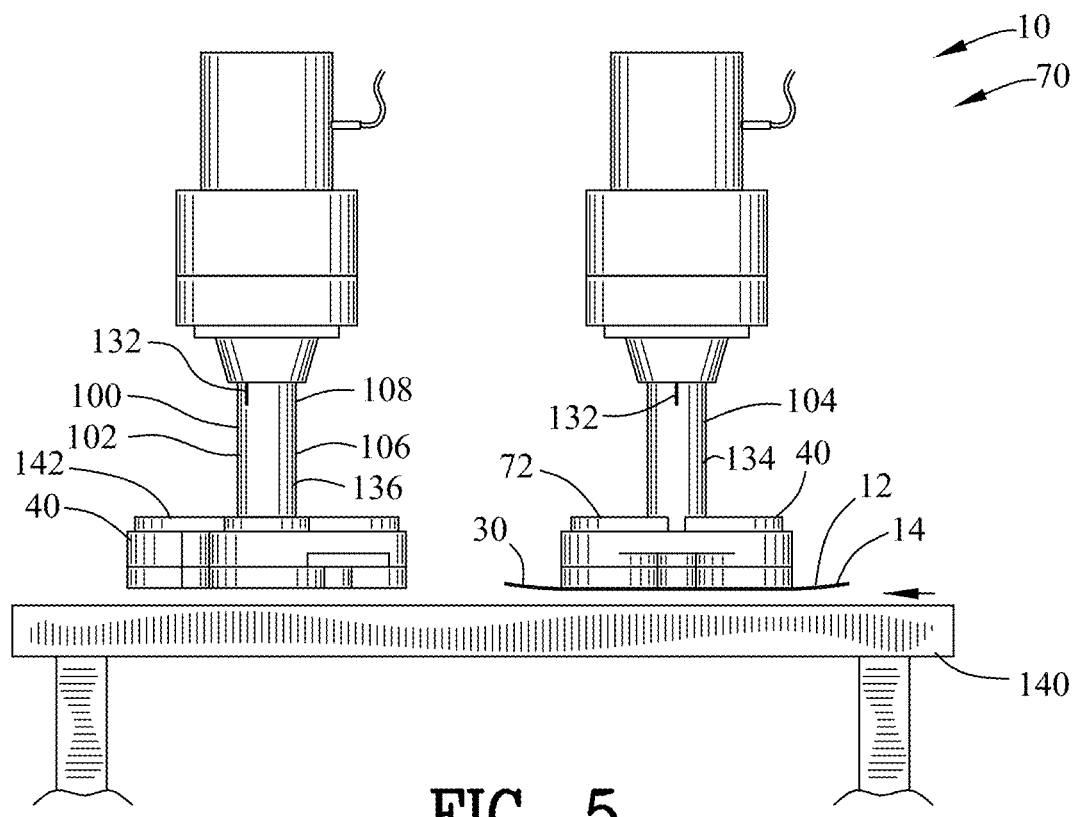
FIG. 5 is a view similar to FIG. 4 illustrating a first base having a first angular orientation relative to the panel body and a vacuum device producing a deformation in the panel body.

FIGS. 4 and 5, illustrate the inspection device 10 including a plurality of base 40 and collar 50 combinations wherein each of the bases 40 and collars 50 have an alternative angular orientation relative to the panel body 12. More specifically, the transfer device 140 transitions the panel body 12 between the base 40 and collar 50 combinations for producing a deep formation in the panel body 12 at alternative angular orientations including the first engagement position 104 and the second engagement position 108. As such, the inspection device 10 as shown in FIGS. 4 and 5 does not require the plurality of base 40 and collar 50 combinations to utilize the base pivot 130.

The base 40 includes a first angular orientation 134 relative to the panel body 12. A base displacer 100 displaces the base 40 relative to the panel body 12. The base displacer 100 converges the base 40 relative to the panel body 12 and the vacuum device 70 evacuates the chamber 58 and deflects the panel body 12 into the chamber 58 for propagating the defect 32 in the panel body 12.

A second chuck 142 with similar structure to the first chuck 72 is positioned adjacent to the first chuck 72. The second chuck 142 includes a second angular orientation 136 relative to the panel body 12. The transfer device 140 positions the panel body 12 from the first chuck 72 to the second chuck 142. The first angular orientation 134 and the second angular orientation 136 define an increased homogeneous stress distribution within the panel body for increasing the area within the panel body for propagating the defect and reducing the evacuation pressure applied by the vacuum device.

By testing the panel body 12 with the combination of the first angular orientation 132 or first panel body deflection 110 and the second angular orientation 136 or the second panel body deflection 120, the inspection device 10 increases the homogeneous stress distribution within the panel body for increasing the area within the panel body for propagating the defect and reducing the evacuation pressure applied by the vacuum device. By utilizing a reduced evacuation pressure applied by the vacuum device, the inspection device 10 avoids damaging the panel body 12.

The subject invention further includes a method for producing a deformation 30 in a panel body 12 and revealing a defect 32 in the panel body 12. As shown in FIGS. 1, 4 and 7 the method comprising the steps of positioning the panel body 12 adjacent to a collar 50 coupled to a base 40 defining a chamber 58. As shown in FIGS. 2, 3, 5 and 9 the chamber 58 is evacuated for deflecting the panel body 12 into the chamber 58 for propagating the defect 32 in the panel body 12.

The vacuum within the chamber 58 is released for removing the panel body 12 from the chamber 58. As shown in FIGS. 1, 4 and 7 the base 40 is separated relative to the panel body 12. The panel body 12 is then inspected for propagated defects 32. The panel body 12 may be inspected for defects 32 by a human eye, microscope 34 such as a scanning acoustic microscope or other inspection devices.

As best shown in FIGS. 3 and 10 the method may further include the step of pivoting the base 40 relative to the panel body 12 for alternating the angular orientation of the base 40 relative to the panel body 12 for defining an alter angular orientation 132 of the base 40 relative to the panel body 12. As shown in FIGS. 2 and 10, the panel body 12 is then positioned adjacent to a collar 50. FIGS. 2, and 10 illustrate the chamber 58 is then evacuated for deflecting the panel body 12 into the chamber 58 for propagating the defect 32 in the panel body 12. The vacuum is then released within the chamber 58 for removing the panel body 12 from the chamber 58. The base 40 is separated relative to the panel body 12. The panel body 12 is then inspected for propagated defects 32.

Figure 30:
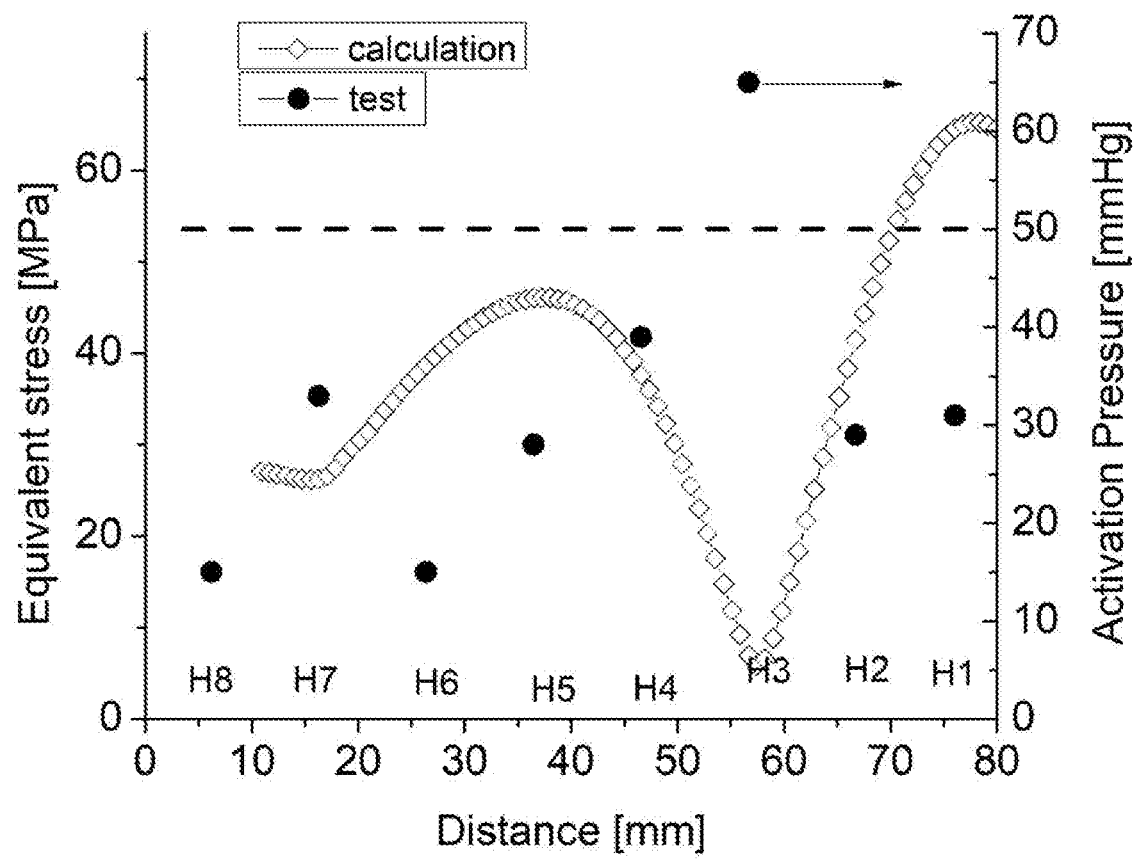
FIG. 30 is a graph showing distribution of calculated equivalent stress (open squares) along the periphery of a square shaped Si wafer and measured data of activation vacuum pressure to elongate a seed crack 32 (closed cracks) positioned along the same line.

FIG. 30 is a plot showing distribution of calculated equivalent stress (open squares) along the periphery of a square shaped Si wafer and measured data of activation vacuum pressure to elongate a seed crack 32 (closed cracks) positioned along the same line. Reverse correlation of stress and pressure is shown. The point H3 falls in the blind area of the wafer 12.

FIGS. 17-29 illustrate an alternative embodiment of the inspection device 10 utilized for inspecting glass 20. The inspection device 10 for produces a deformation in a panel body 12 and reveals a defect in the panel body 12. The panel body 12 including a primary panel 24 and a secondary panel 26.

As shown in FIGS. 17-20, the inspection device 10 comprises a primary base 150 having an upper surface 152 and a lower surface 154. A primary collar 160 has an upper surface 162, a lower surface 164 and defines an opening 166. The lower surface 164 of the primary collar 160 is coupled to the upper surface 152 of the primary base 150 for defining a primary chamber 168. A vacuum device 170 is connected with the primary chamber 168 for evacuating the primary chamber 168 after the primary panel 24 is positioned adjacent to the upper surface 162 of the primary collar 60 and deflects the primary panel 24 into the primary chamber 168 for propagating the defect 32 in the panel body 12.

FIGS. 21-24, illustrate a secondary base 180 having an upper surface 182 and a lower surface 184. A secondary collar 190 has an upper surface 192, a lower surface 194 and defines an opening 196. The lower surface 194 of the secondary collar 190 is coupled to the upper surface 182 of the secondary base 180 for defining a secondary chamber 198.

The vacuum device 170 is connected with the secondary chamber 198 for evacuating the secondary chamber 198 after the secondary panel 26 is positioned adjacent to the upper surface 192 of the secondary collar 190 and deflects the secondary panel 26 into the secondary chamber 198 for propagating the defect 32 in the panel body 12.

The primary collar 160 may include a deformable material 210 for defining a primary deflection seal 212 between the primary collar 160 and the panel body 12 for maintaining a vacuum within the primary chamber 168 during deflecting the panel body 12 into the primary chamber 168. The deformable material 210 may include foam having a closed or opened porosity, polymer or other semi-rigid materials.

The secondary collar 190 may similarly include a deformable material 220 for defining a secondary deflection seal 222 between the secondary collar 190 and the panel body 12 for maintaining a vacuum within the secondary chamber 198 during deflecting the panel body 12 into the secondary chamber 198. The deformable material 220 may include foam having a closed or opened porosity, polymer or other semi-rigid materials.

A primary screen 214 may be positioned adjacent to the upper surface 162 of the primary collar 160 for retaining fragments of the primary panel 24 that were separated from the primary panel 24 during deflection and prevents the fragments from entering the primary chamber 168 and the vacuum device 170. The primary screen 214 may alternatively be positioned between the primary collar 160 and the primary base 150 for retaining fragments of the primary panel 24 that were separated from the primary panel 24 during deflection and prevents the fragments from entering the primary chamber 168 and the vacuum device 170.

A secondary screen 224 may be positioned adjacent to the upper surface 192 of the secondary collar 190 for retaining fragments of the secondary panel 26 that were separated from the secondary panel 26 during deflection and prevents the fragments from entering the secondary chamber 198 and the vacuum device 170. The secondary screen 224 may alternatively be positioned between the secondary collar 190 and the secondary base 180 for retaining fragments of the secondary panel 26 that were separated from the secondary panel 26 during deflection and prevents the fragments from entering the secondary chamber 198 and the vacuum device 170.

Figure 29:
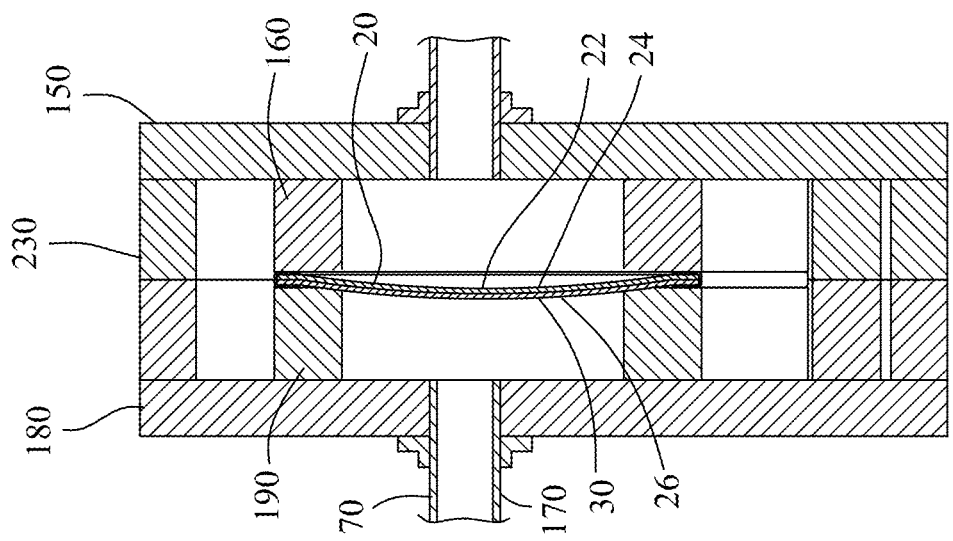
FIG. 29 is a similar view to FIG. 27 illustrating the vacuum device evacuating a secondary chamber and deflecting the secondary panel.
Figure 28:
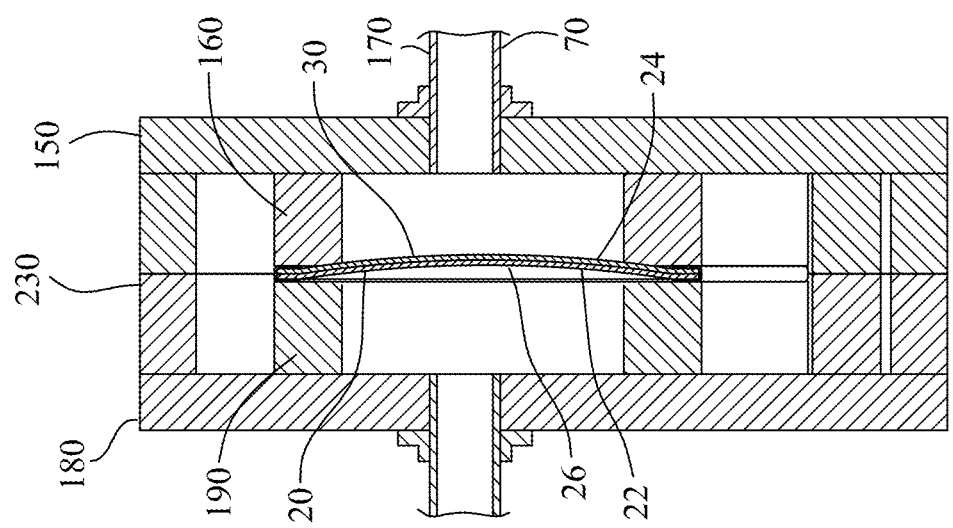
FIG. 28 is a view similar to FIG. 27 illustrating the vacuum device evacuating a primary chamber and deflecting the primary panel.

FIGS. 25-29 illustrate the primary base 150 and the secondary base 180 configured into a plurality of abutting layers 230 for sequentially testing the panel body 12 between the primary panel 24 and the primary base 150 as shown in FIG. 28 and then between the secondary panel 26 and the secondary base 180 as shown in FIG. 29.

Figure 27:
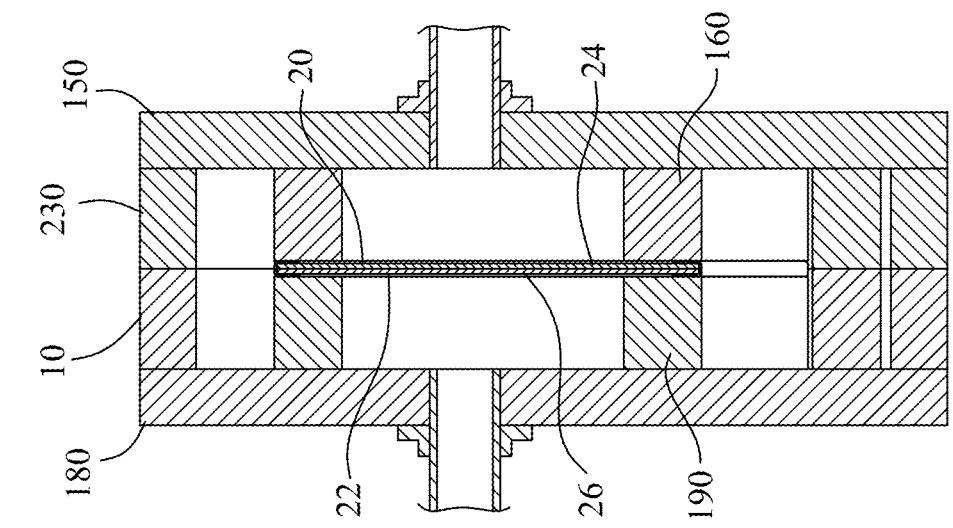
FIG. 27 is a sectional view along line 27-27 in FIG. 25.

The subject invention further includes a method for producing a deformation in the primary panel 24 and the secondary panel 26 and revealing a defect 32 in the panel body 12. As shown in FIGS. 18, 19 and 27, the method comprises the steps of positioning the primary panel 24 adjacent to a primary collar 160 coupled to a primary base 150 defining a primary chamber 168. FIGS. 20 and 28 illustrates the primary chamber 168 being evacuated for deflecting the primary panel 24 into the primary chamber 168 for propagating the defect 32 in the primary panel 24. The vacuum 170 is released within the primary chamber 168 for removing the primary panel 24 from the primary chamber 168.

Figure 23:
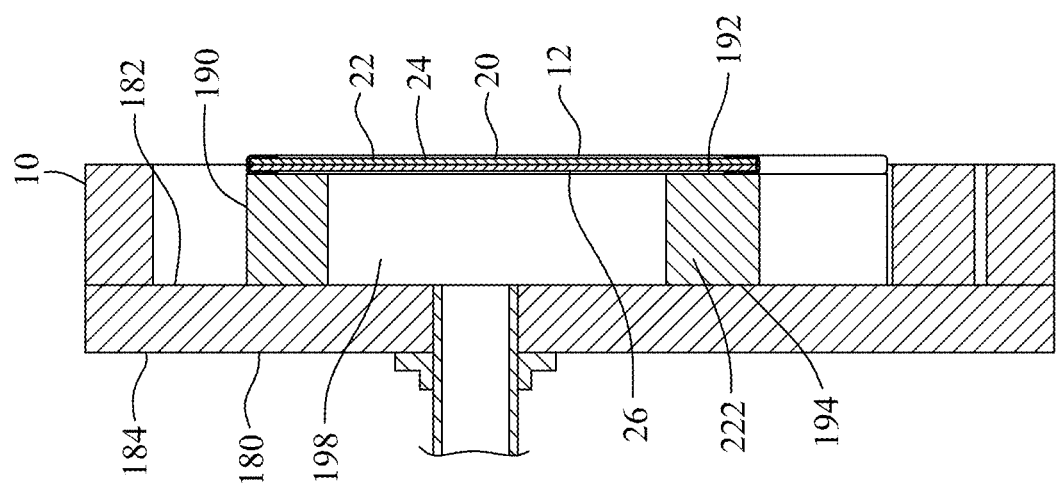
FIG. 23 is a sectional view along line 23-23 in FIG. 22.
Figure 24:
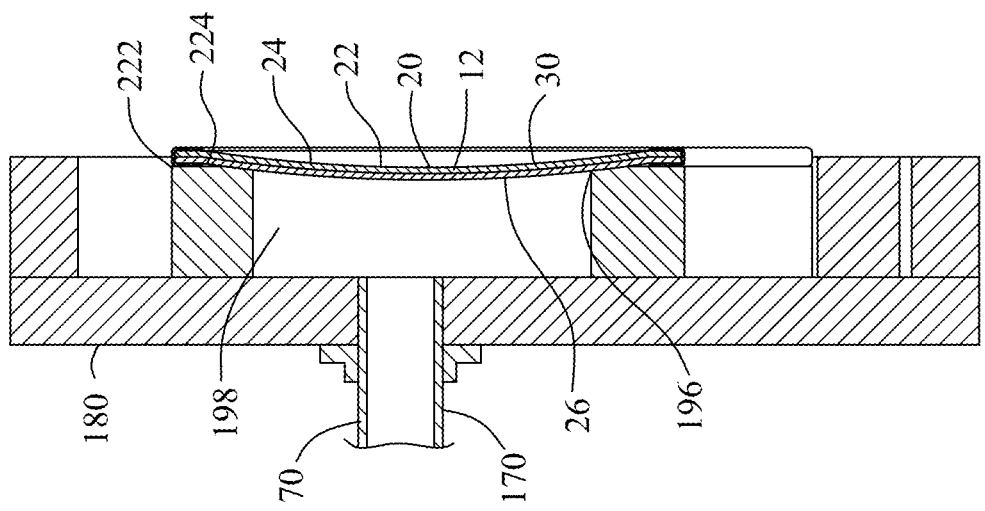
FIG. 24 is a view similar to FIG. 23 illustrating the vacuum device evacuating a secondary chamber and deflecting the secondary panel.

As shown in FIGS. 22, 23 and 27, the secondary panel 26 is then positioned adjacent to a secondary collar 190 coupled to a secondary base 180 defining a secondary chamber 198. FIGS. 24 and 29, illustrate the secondary chamber 198 being evacuated for deflecting the secondary panel 26 into the secondary chamber 198 for propagating the defect 32 in the secondary panel 26. The vacuum 170 is released within the secondary chamber 198 for removing the secondary panel 26 from the secondary chamber 198. The panel body 12 is then inspected for propagated defects 32.

Figure 31:
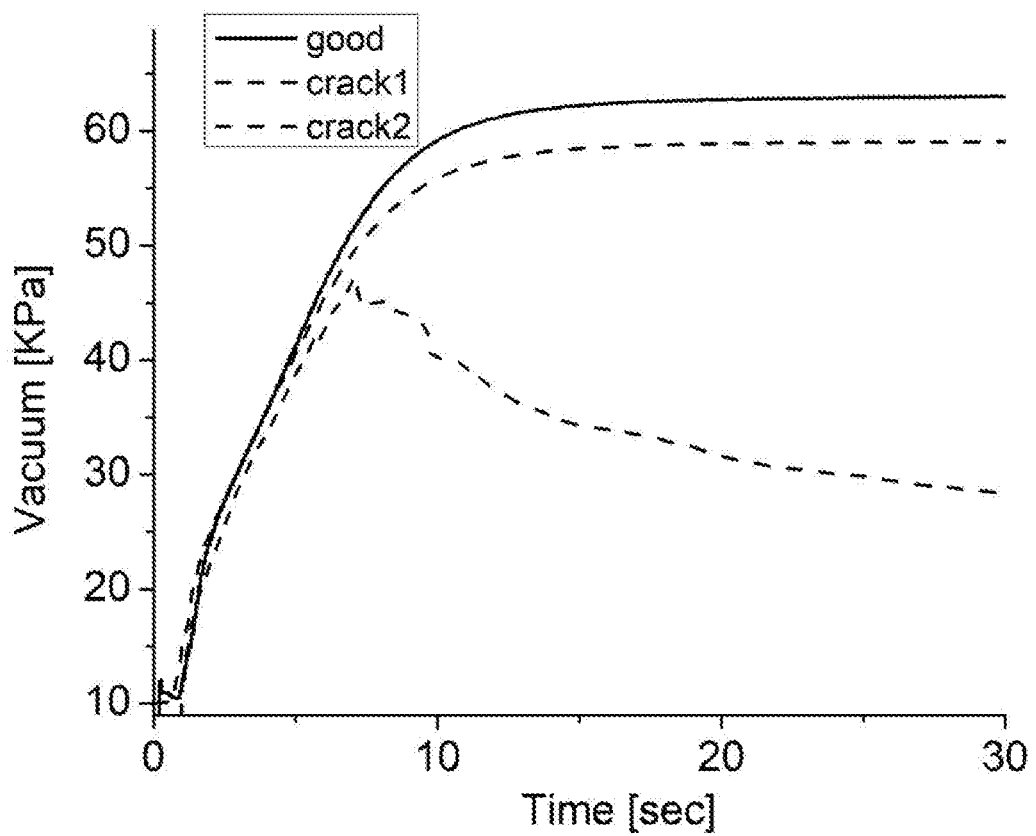
FIG. 31 is a graph showing vacuum profile of a good window and a damaged window.

FIG. 31 is a plot of vacuum profile increase after turning vacuum on. After initial raise during first 10 seconds the vacuum pressure is stabilized at −60 KPa for good window (solid line). If windows have cracks the vacuum level is lower due to leak through elongated window damage (dashed line).

The present disclosure includes that contained in the appended claims as well as the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. An inspection device for producing a deformation in a panel body and revealing a defect in the panel body, comprising:
   a base,
   a collar extending from said base for defining an opening and a chamber;
   a vacuum device connecting with said chamber for evacuating said chamber after the panel body is positioned adjacent to an upper surface of said collar and deflecting the panel body into said chamber for propagating the defect in the panel body;
   a base displacer for displacing said base relative to the panel body;
   a base pivot pivoting said base relative to the panel body during said base displacer separating said base relative to the panel body for defining an alter angular orientation of said base relative to the panel body; and said base displacer converging said base relative to the panel body and said vacuum device evacuating said chamber and deflecting the panel body into said chamber for propagating the defect in the panel body.

2. The inspection device as set forth in claim 1, wherein said collar includes a quatrefoil shape for symmetrically deflecting the panel body into said chamber.

3. The inspection device as set forth in claim 1, further including a deformable material abutting said collar for defining a deflection seal between said collar and the panel body for maintaining a vacuum within said chamber during deflecting the panel body into said chamber.

4. The inspection device as set forth in claim 3, wherein said deformable material includes a quatrefoil shape for symmetrically sealing between said collar and the panel body for maintaining a vacuum within said chamber during deflecting the panel body into said chamber.

5. The inspection device as set forth in claim 1, further including a screen abutting said collar for retaining fragments of the panel body that were separated from the panel body during deflection and preventing the fragments from entering said chamber and said vacuum device.

6. An inspection device for producing a deformation in a wafer and revealing a defect in the wafer, comprising:
a base
a collar extending from said base for defining an opening and a chamber;
a vacuum device connecting with said chamber for evacuating said chamber after the wafer is positioned adjacent to said upper surface of said collar and deflecting the wafer into said chamber for propagating the defect in the wafer;
a base displacer for positioning said wafer between a first engagement position, a non-engagement position and a second engagement position;
said first engagement position abutting the wafer with said base for defining a first wafer deflection upon said vacuum device evacuating said chamber;
said non-engagement position separating said base relative to the wafer;
a base pivot pivoting said base relative to the wafer during said non-engagement position for alternating the angular orientation of said base relative to the wafer for defining an alter angular orientation of said base relative to the wafer;
said second engagement position abutting the wafer with said base for defining a second wafer deflection upon said vacuum device evacuating said chamber; and
said first wafer deflection and said second wafer deflection defining an increased homogeneous stress distribution within the wafer for increasing the area within the wafer for propagating the defect and reducing the evacuation pressure applied by said vacuum device.

7. The inspection device as set forth in claim 6, wherein said collar includes a quatrefoil shape for symmetrically deflecting the wafer into said chamber.

8. The inspection device as set forth in claim 6, further including a deformable material abutting said collar for defining a deflection seal between said collar and the wafer for maintaining a vacuum within said chamber during deflecting the wafer into said chamber.

9. The inspection device as set forth in claim 8, wherein said deformable material includes a quatrefoil shape for symmetrically sealing between said collar and the wafer for maintaining a vacuum within said chamber during deflecting the wafer into said chamber.

10. The inspection device as set forth in claim 6, further including a screen abutting said collar for retaining fragments of the wafer that were separated from the wafer during deflection and preventing the fragments from entering said chamber and said vacuum device.

11. A method for producing, a deformation in a panel body and revealing a defect in the panel body, the method comprising the steps of:
positioning the panel body adjacent to a collar coupled to a base defining a chamber;
evacuating the chamber for deflecting the panel body into the chamber for propagating the defect in the panel body;
releasing the vacuum within the chamber for removing the panel body from the chamber;
separating said base relative to the panel body;
inspecting the panel body for propagated defects;
pivoting the base relative to the panel body for alternating the angular orientation of the base relative to the panel body for defining an alter angular orientation of the base relative to the panel body;
positioning the panel body adjacent to the collar;
evacuating the chamber for deflecting the panel body into the chamber for propagating the defect in the panel body;
releasing the vacuum within the chamber for removing the panel body from the chamber;
separating said base relative to the panel body; and
inspecting the panel body for propagated defects.

12. An inspection device for producing a deformation in a panel body and revealing a defect in the panel body, comprising:
a base;
a collar extending from said base for defining an opening and a chamber;
a vacuum device connecting with said chamber for evacuating said chamber after the panel body is positioned adjacent to said upper surface of said collar and deflecting the panel body into said chamber for propagating the defect in the panel body;
a base displacer for positioning said panel body between a first engagement position, a non-engagement position and a second engagement position;
said first engagement position abutting the panel body with said base for defining a first panel body deflection upon said vacuum device evacuating said chamber;
said non-engagement position separating said base relative to the panel body;
a base pivot pivoting said base relative to the panel body during said non-engagement position for alternating the angular orientation of said base relative to the panel body for defining an alter angular orientation of said base relative to the panel body;
said second engagement position abutting the panel body with said base for defining a second panel body deflection upon said vacuum device evacuating said chamber; and
said first panel body deflection and said second panel body deflection defining an increased homogeneous stress distribution within the panel body for increasing the area within the panel body for propagating the defect and reducing the evacuation pressure applied by said vacuum device.

13. An inspection device for producing a deformation in a panel body and revealing a defect in the panel body, comprising:
- a base;
- a collar extending from said base for defining an opening and a chamber;
- a vacuum device connecting with said chamber for evacuating said chamber after the panel body is positioned adjacent to said upper surface of said collar and deflecting the panel body into said chamber for propagating the defect in the panel body;
- a displacer for separating said base and the panel body;
- a pivot for defining an alter angular orientation of said base and the panel body; and
- said displacer converging said base and the panel body and said vacuum device evacuating said chamber and deflecting the panel body into said chamber for propagating the defect in the panel body.

14. A method for producing a deformation in a panel body and revealing a defect the panel body, the method comprising the steps of:

converging the panel body and a collar coupled to a base defining a chamber;

evacuating the chamber for deflecting the panel body into the chamber for propagating the defect in the panel body;

releasing the vacuum within the chamber for removing the panel body from the chamber;

separating said base and the panel body:

pivoting for alternating the angular orientation of the collar and the panel body;

converging the panel body and the collar;

evacuating the chamber for deflecting the panel body into the chamber for propagating the defect in the panel body;

releasing the vacuum within the chamber for removing the panel body from the chamber;

separating said base and the panel body; and inspecting the panel body for propagated defects.

* * * * *